US 6,689,265 B2

(12) United States Patent
Heller et al.

(10) Patent No.: US 6,689,265 B2
(45) Date of Patent: *Feb. 10, 2004

(54) ELECTROCHEMICAL ANALYTE SENSORS USING THERMOSTABLE SOYBEAN PEROXIDASE

(75) Inventors: Adam Heller, Austin, TX (US); Gregg L. Kenausis, Austin, TX (US); Qiang Chen, Austin, TX (US); Mark S. Vreeke, Alameda, CA (US)

(73) Assignee: TheraSense, Inc., Alameda, CA (US)

(*) Notice: Subject to any disclaimer, the term of this patent is extended or adjusted under 35 U.S.C. 154(b) by 131 days.

This patent is subject to a terminal disclaimer.

(21) Appl. No.: 09/815,747

(22) Filed: Mar. 23, 2001

(65) Prior Publication Data

US 2001/0017269 A1 Aug. 30, 2001

Related U.S. Application Data

(63) Continuation of application No. 09/291,230, filed on Apr. 13, 1999, now abandoned, which is a continuation of application No. 08/798,596, filed on Feb. 11, 1997, now Pat. No. 5,972,199, which is a continuation-in-part of application No. 08/540,789, filed on Oct. 11, 1995, now Pat. No. 5,665,222.

(51) Int. Cl.[7] ............................................. G01N 27/327
(52) U.S. Cl. ........................ 204/403.09; 204/403.04; 204/403.14
(58) Field of Search ....................... 204/403.04, 403.09, 204/403.1, 403.11, 403.14

(56) References Cited

U.S. PATENT DOCUMENTS 3,781,212 A   12/1973  Smillie
3,796,634 A    3/1974  Haynes et al.

(List continued on next page.)

FOREIGN PATENT DOCUMENTS

EP   0 390 390 A1   10/1990
EP   0 439 318 A2    7/1991

(List continued on next page.)

OTHER PUBLICATIONS

User's Manual for YSI 2300 Stat Plus Glucose & L–Lactate Analyzer, Yellow Springs Instruments, Inc. Yellow Springs, Ohio, believed available before Oct. 1995.*

Liu et al., "Reagentless amperometric biosensors highly sensitive . . . mediator between horseradish peroxidase and an electrode," Analytica Chimica Acta 344 (1997) 187–199.*

(List continued on next page.)

Primary Examiner—Alex Noguerola
(74) Attorney, Agent, or Firm—Merchant & Gould P.C.

(57) ABSTRACT

A sensor for the detection and measurement of an analyte in a biofluid. The sensor includes two enzymes. One type of sensor measures the concentration of hydrogen peroxide using a thermostable peroxidase enzyme that is immobilized in a redox hydrogel to form a sensing layer on a working electrode. This sensor also includes a hydrogen peroxide-generating second enzyme which is insulated from the redox hydrogel and electrode. This second enzyme generates hydrogen peroxide in response to the presence of an analyte or analyte-generated compound. The second enzyme may be insulated from the electrode by placement of an electrically insulating layer between the sensing layer and the second enzyme layer.

Alternatively, the second enzyme is immobilized in an inorganic polymeric matrix, preferably made using a sol-gel polymerization process. Such matrices include those made of silica. Often, the second enzyme is stabilized by immobilization in a sol-gel. Further stabilization of polyelectrolytic enzymes can be obtained by immobilizing the enzyme with a polyelectrolytic polymer in the sol-gel matrix.

20 Claims, 20 Drawing Sheets

U.S. PATENT DOCUMENTS

| | | | |
|---|---|---|---|
| 3,911,901 A | | 10/1975 | Niedrach et al. |
| 4,102,746 A | | 7/1978 | Goldberg |
| 4,458,686 A | | 7/1984 | Clark, Jr. |
| 4,781,798 A | | 11/1988 | Gough |
| 4,840,893 A | | 6/1989 | Hill et al. |
| 4,938,860 A | | 7/1990 | Wogoman |
| 5,165,407 A | | 11/1992 | Wilson et al. |
| 5,240,843 A | | 8/1993 | Gibson et al. |
| 5,264,092 A | | 11/1993 | Skotheim et al. |
| 5,278,046 A | | 1/1994 | Johnson et al. |
| 5,292,801 A | | 3/1994 | Avnir et al. |
| 5,300,564 A | | 4/1994 | Avnir et al. |
| 5,308,495 A | | 5/1994 | Avnir et al. |
| 5,320,725 A | | 6/1994 | Gregg et al. |
| 5,334,296 A | | 8/1994 | Henkens et al. |
| 5,352,348 A | | 10/1994 | Young et al. |
| 5,643,721 A | | 7/1997 | Spring et al. |
| 5,665,222 A | * | 9/1997 | Heller et al. ............... 205/792 |
| 5,964,993 A | | 10/1999 | Blubaugh, Jr. |
| 5,972,199 A | * | 10/1999 | Heller et al. ............ 205/777.5 |

FOREIGN PATENT DOCUMENTS

| | | |
|---|---|---|
| JP | 62155099 | 7/1987 |
| JP | 02087056 | 3/1990 |
| JP | 02268684 | 11/1990 |
| RU | 2 049 991 | 12/1995 |
| WO | WO 93/20230 | 10/1993 |
| WO | WO 93/23748 | 11/1993 |
| WO | WO 95/10605 | 4/1995 |
| WO | WO 97/13870 | 4/1997 |

OTHER PUBLICATIONS

Liu et al., "Entrapment of both glucose oxidase and peroxidase in regenerated silk fibroin membrane," Fresenius J. Anal. Chem. (1996) 355, 78–82.*

Chuang et al., "Purification and Characterization of Vegetable Soybean Peroxidase (II). CHaracterization of Vegetable Soybean Peroxidase Isoenzymes," Shih P'in K'o Hsueh (Taipei) (1988), 15(1), 12–26.*

Aharonson et al., Recent Developments in Organically Doped Sol–Gel Sensors: A Microns–Scale Probe: Successful Trapping of Purified Polyclonal Antibodies; Solutions to the Dopant–Leaching Problem, in "Better Ceramics Through Chemistry", Sanchez et al. Eds. Materials Res. Soc. Symp. Proc., 346:1–12 (1994).

Alvarez–Icaza, et al., Mass Production of Biosensors, Anal. Chem., 65:525A–533A (1993) Jun. 1, 1993.

Asther et al., Immobilization as a Tool for the Stabilization of Lignin Peroxidase Produced by Phanerochaete chrysosporium INA–12, Applied Biochemisry and Biotechnology, 38:57–67 (1992).

Audebert, et al., Electrochemical Probing of the Activity of Glucose Oxidase Embedded Sol–Gel Matrices, Chem. Mater, 5:911–913 (1993).

Avnir, et al., Enzymes and Other Proteins Entraped in Sol–Gel Materials, Chem. Mater., 6:1605–1614 (1994).

Avnir, Organic Chemistry within Ceramic Matrices: Doped Sol–Gel Materials, Acc. Chem. Res., 28:328–334 (1995).

Braun, et al., Biochemically active sol–gel glasses; the trapping of enzymes, Materials Letters, 10:1–5 (1990).

Chien, et al., An immobilized–enzyme system for the determination of sialic acid using cloned neuraminidase from Clostridium perfringens A.T.C.C. 10543, Biotechnol. Appl. Biochem., 19:51–60 (1994).

Csoregi et al., Design, Characterization and One–point in Vivo Calibration of a Subcutaneously Implanted Glucose Electrode, Anal. Chem., 66, 3131–3138 (1994).

Dave et al., Synthesis of Protein–Doped Sol–Gel SiO2 Thin Films: Evidence for Rotational Mobility of Encapsulated Cytochrome, Chem. Mater., 7:1431–1434 (1995).

Ellerby, et al., Encapsulation of Proteins in Transparent Porous Silicate Glasses Prepared by the Sol–Gel Method, Science, 255:1113–1115 (1992).

Enzymol International, Inc. 2543 Westbelt Dr., Columbus, OH 43228, Product Literature Oct. 1995.

Fukushima, et al., A New Immobilization Technique of Whole Cells and Enzymes with Colloidal silica and Alginate, Biotechnology and Bioengineering, 32:584–594 (1988).

Gibson et al, Stabilization of Analytical Enzymes Using a Novel Polymer–Carbohydrate System and the Production of a Stabilized, Single Reagent for Alcohol Analysis, Analyst, 117:1293–1297 (1992).

Gibson et al., Extended shelf life of enzyme–based biosensors using a novel stabilization system, Biosensors & Bioelectronics, 7:701–708 (1992).

Gibson et al., Preservation of shelf life of enzyme based analytical systems using a combination of sugars, sugar alcohols and cationic polymers of zinc ions, Analytica Chimic Acta, 279:185–192 (1993).

Gibson et al., The Stabilization of Analytical Enzymes Using Polyelectrolytes and Sugar Derivatives, in "Stability and Stabilization of Enzymes", van den Tweel et al. Eds., Elsevier Science Publishers B.V. (1993).

Gorton et al., Selective detection in flow analysis based on the combination of immobilized enzymes and chemically modified electrodes, Analytica Chimica Acta, 250:203–248 (1991).

Gregg, et al., Redox Polymer Films Containing Enzymes. 1. A Redox–Conducting Epoxy Cement: Synthesis, Characterization, and Electrocatalytic Oxidation of Hydroquinone, J. Phys. Chem., 95:5970–5975 (1991).

Hatayama, et al., Immobilizaiton of Urease on Composite Fibre by Using a Gel Formation of Cellulose Acetate and Titanium Iso–Propxide, Journal of Sol–Gel Science and Technology 7:13–17 (1996).

Haynes, et al., Enzyme Envelopes on Colloidal Particles, Biochemical and Biophysical Research Communications, 36:235–242 (1969).

Kallury, et al., Enhanced Stability of Urease Immobilized onto Phospholipid Covelently Bound to Silica Tungsten, and Fluoropolymer Surfaces, Anal. Chem., 65:2459–2467 (1993) Sep. 15, 1993.

Kallury, et al., Enhancement of the Thermal and Storage Stability of Urease by Covalent Attachment to Phospholipid–Bound Silica, Anal. Chem., 64:1062–1068 (1992) May 1, 1992.

Katakis, et al., Electrostatic Control of the Electron Transfer Enabling Binding of Recombinant Glucose Oxidase and Redox Polyelectrolytes, J. Am. Chem. Soc., 116:3617–3618 (1994).

Katsube et al., "Stabilization of an FET Glucose Sensor with the Thermophilic Enzyme Glucokinase", Sens. Actuators, B (1990), B1(1–6), 504–7.

Kenausis, G., "Electrochemical Gluclose and Lactate Sensors Based on "Wired" Thermostable Soybean Peroxidase Operating Continuously and Stabley at 37° C.", Anal. Chem., 69(6):1054–1060 (Mar. 15, 1997).

Kulys, et al., Mediatorless peroxidase electrode and preparation of bienzyme sensors, Bioelectrochemistry and Bioenergetics, 24:305–311 (1994).

Marcinkeviciene, J. et al., "Bienzyme Strip–type Glucose Sensor", *Biosensors & Bioelectronics,* 8:209–212 (1993).

McNeil, et al., Thermostable Reduced Nicotinamide Adenine Dinucleotide Oxidase: Application To Amperometric Enzyme Assay, Anal. Chem., 61:25–29 (1989).

Paddock, et al., Electrocatalytic reduction of hydrogen peroxide via direct electron transfer from pyrolytic graphite electrodes to irreversibly absorbed cytochrome c peroxidase, J. Electoanal. Chem., 260:487–494 (1989).

Pankratov et al., Sol–gel derived renewable–surface biosensors, Journal of Electroanalytical Chemistry, 393:35–41 (1995).

Ryan, et al., Thermostabilized chemical derivatives of horseradish peroxidase, Enzyme Microb. Technol., 16:501–505 (1994).

Sampath, et al. Sol–Gel Derived Ceramic–Carbon Enzyme Electrodes: Glucose Oxidase as a Test Case, Journal of Sol–Gel Science and Technology, 7:123–128 (1996).

Shtelzer et al., An optical biosensor based upon glucose oxidase immobilized in sol–gel silicate matrix, Biotechnol. Appl. Biochem., 19:293–305 (1994).

Suekane, Immoblization of glucose isomerase, Zeitschrift fur Allgemeine Mikrobiologie, 22:565–576 (1982).

Tatsuma, et al., Enzyme Monolayer and Bilayer–Modified Tin Oxide Electrodes for the Determination of Hydrogen Peroxide and Glucose, Anal. Chem., 61:2352–2355 (1989).

Vreeke, et al., Hydrogen Peroxide and β–Nicotinamide Adenine Dinucleotide Sensing Amperometric Electrodes Based on Electrical Connection of Horseradish Peroxidase Redox Centers to Electrodes through a Three–Dimensional Electron Relaying Polymer Network, Anal. Chem., 64:3084–3090 (1992).

Vreeke, et al., Hydrogen Peroxide Electrodes Based on Electrical connection of Redox Centers of Various Peroxidases to Electrodes through a Three–Dimensional Electro–Relaying Polymer Network, in "Diagnostic Biosensor Polymers" ACS Symposium Series 556:180–193 (1994).

Vreeke, M.S. et al., "A Thermostable Hydrogen Peroxide Sensor Based on "Wiring" of Soybean Peroxidase", *Anal. Chem.,* 67(23):4247–4249 (Dec. 1, 1995).

Wang et al., Screen–Printable Sol–Gel Enzyme–Containing Carbon Inks, Anal. Chem., 68:2705–2708 (1996).

Wang et al., Sol–Gel–Derived Metal–Dispersed Carbon Composite Amperometric Biosensors, Electroanalysis, 9:52–55 (1997).

Wang, et al., Amperometric biosensing of organic peroxides with peroxidase–modified electrodes, Anal. Chim. Acta, 254:81–88 (1991).

Weetall, Storage Stability of Water–Insoluble Enzymes Covalently Coupled to Organic and Inorganic Carriers, Biochim. Biophys. Acta. 212:1–7 (1970).

Yamanaka, et al., Enzymatic Activity of Glucose Oxidase Encapsulated in Transparent Glass by the Sol–Gel Method, Chem. Mater, 4:495–497 (1992) May/Jun.

Yang, et al., Applications of "Wired" Peroxidase Electrodes for Peroxide Determination in Liquid Chromatography Coupled to Oxidase Immobilized Enzyme Reactors, Anal. Chem., 67:1326–1331 (1995).

Ye et al., Influence of additives on the thermostability of glucose oxidase, Enzyme Microb. Technol., 10:498–502 1988).

Zaitseva, et al., Stabilization of heterogeneous amylose catalysts, Russian Journal of Physical Chemistry 66:1662–1664 (1992).

Zusman et al., Doped Sol–Gel Glasses as Chemical Sensors, Journal of Non–Crystalline Solids, 122:107–109 (1990).

* cited by examiner

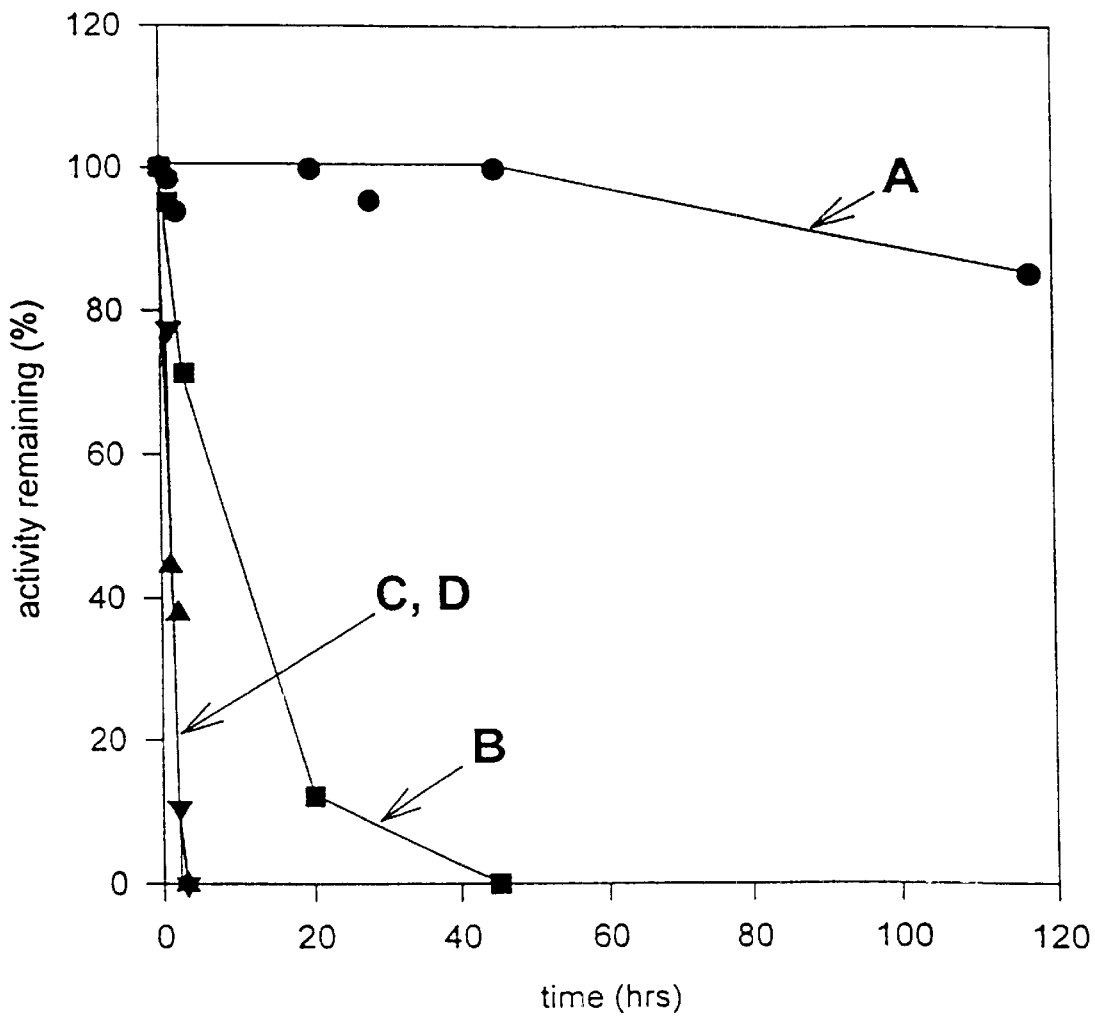

ELECTROCHEMICAL ANALYTE SENSORS USING THERMOSTABLE SOYBEAN PEROXIDASE

This application is a continuation application under 37 CFR §1.53(b) of Ser. No. 09/291,230, filed on Apr. 13, 1999, now abandoned, which is a continuation of U.S. patent application Ser. No. 08/798,596 filed on Feb. 11, 1997, U.S. Pat. No. 5,972,199, which is a continuation-in-part of U.S. patent application Ser. No. 08/540,789 filed Oct. 11, 1995, U.S. Pat. No. 5,665,222, which application(s) are incorporated herein by reference.

FIELD OF THE INVENTION

The present invention relates to thermostable analyte sensors. More particularly, the invention relates to electrochemical sensors for the measurement of bioanalytes such as glucose and lactate. The inventive sensors include a thermostable peroxidase, such as soybean peroxidase, disposed on an electrode in a redox-compound-containing film. The sensor further includes a hydrogen peroxide-producing enzyme. The inventive sensors, for example in the measurement of blood glucose or lactate, operate for five days or more at 37° C., losing less than 10% of their sensitivity during continuous or intermittent operation.

BACKGROUND OF THE INVENTION

The assay of biochemicals, such as glucose and lactate, is important in medicine, biotechnology, and food processing (dairy and wine). Monitoring of glucose concentrations in fluids of the human body is of particular relevance to diabetes management. Monitoring of lactate in fluids of the human body is of relevance to diagnosis of trauma, of myocardial infarction, congestive heart failure, pulmonary edema, septicemia, hemorrhage, and others. Blood lactate levels above 7–8 mM are indicative of a fatal outcome. Bedside analyzers of lactate are useful in determining the response of patients to treatment, while in accidents and battle, they are useful in triage. Glucose assays are common in clinical practice and are applied in the diagnosis of Diabetes Mellitus and its management. Continuously or intermittently operating glucose sensors, including sensors implanted in the human body, are sought for the management of Type I diabetes, for example, for warning of imminent or actual hypoglycemia and its avoidance. Hypoglycemia can be fatal. For maintenance of diabetic patients at or near normal blood glucose levels, frequent or continuous monitoring of glucose is needed. Today, most Type I diabetic patients maintain their blood glucose at higher than normal levels, so as to reduce risk of fatal hypoglycemia. This is undesirable, as maintenance of higher than normal blood glucose levels has been shown to be a leading cause of blindness, kidney failure, neuropathy, and other complications of diabetes. It would, therefore, be useful to provide a glucose sensor that operates continuously or intermittently for a prolonged period of time to measure glucose in body fluid at 37° C. without substantial loss of sensitivity.

The present invention discloses material, structures, and methods enabling continuous operation of electrochemical sensors, for example, measuring glucose for more than one week or measuring lactate for more than 100 hours, with less than 10% loss in sensitivity.

SUMMARY OF THE INVENTION

Novel electrochemical sensors are presented, some of which are capable of operating at 37° C. continuously or intermittently, measuring biochemicals in body fluids with less than 10% loss of sensitivity in more than 100 hours of operation are described herein. The inventive sensors are relatively insensitive to electrooxidizable interferants, including ascorbate and acetaminophen.

The sensors of the invention include at least two enzymes, a thermostable peroxidase, such as soybean peroxidase, and a peroxidase-generating enzyme. In a preferred embodiment, redox centers of a thermostable peroxidase are electroreduced by electrons transported from a working electrode through a redox hydrogel in which the thermostable peroxidase is immobilized, preferably at a potential negative of 0.4 V versus the standard calomel electrode (SCE) and positive of −0.15 V (vs SCE). Most preferably, the thermostable peroxidase is coated on the electrode at a potential near 0.0V (vs SCE).

The preferred redox hydrogel comprises at least 20% by weight of water when in contact with a fluid to be assayed, and its redox centers are not leached by the assay fluid at 37° C. Non-leachable redox centers are bound to a polymer that forms the hydrogel upon water uptake. Preferably, the binding to the polymer is through covalent, electrostatic/ionic, or coordination bonds.

The redox centers of the peroxide-generating enzyme are preferably electrically insulated from the electrode, from the redox centers of the thermostable peroxidase, and from the redox centers of the redox hydrogel. The electrically insulated, peroxide-generating enzyme catalyzes reaction of a biochemical analyte, e.g., glucose or lactate, or a product of the analyte, with molecular oxygen. In the oxidation reaction, oxygen is reduced to hydrogen peroxide ($H_2O_2$).

The hydrogen peroxide-generating enzyme is preferably stabilized in a matrix. The preferred stabilizing matrices are macromolecular and inorganic. The most preferred matrices include silicon atoms, at least 50% of which are covalently linked to neighboring oxygen atoms, which are formed into a three-dimensional, crosslinked network. Such matrices can be made using a sol-gel polymerization process. The stabilizing matrix optionally includes a second polymer, which functions to further stabilize the insulated, peroxide-generating enzyme.

The peroxide-generating enzyme is preferably positioned behind or immobilized in a polymer that is at least tenfold, and preferably at least 100-fold, more permeable to oxygen than is the biochemical analyte to be measured. Examples of such polymers include silicone rubbers, produced by crosslinking a poly(dimethyl siloxane) derivative and cellulose acetate.

BRIEF DESCRIPTION OF THE FIGURES

Referring now to the drawings, wherein like reference numerals and letters indicate corresponding structure throughout the several views and where Examples 2–12 are for sensors described in Example 1.

Figure 4:
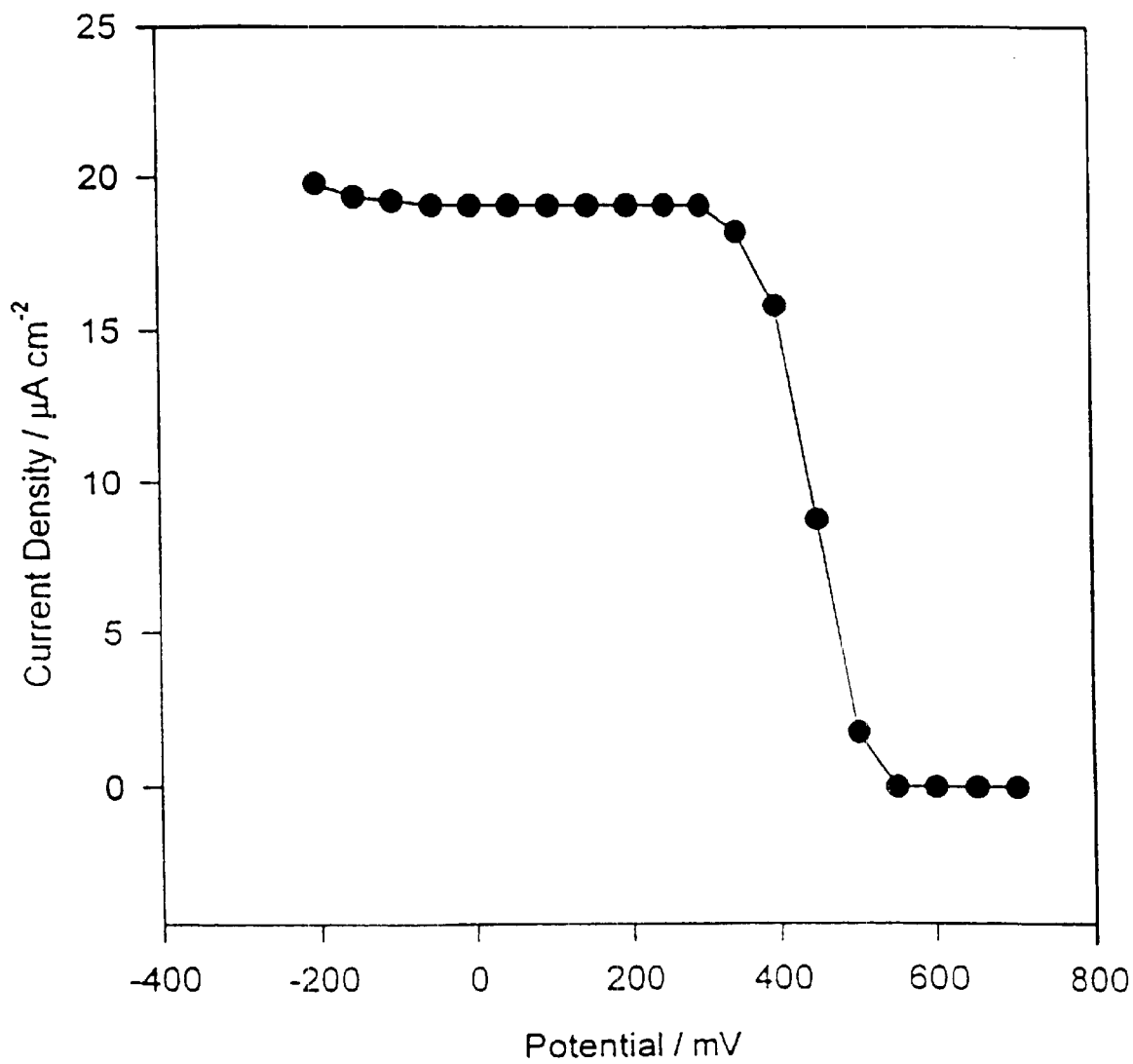
Figure 5:
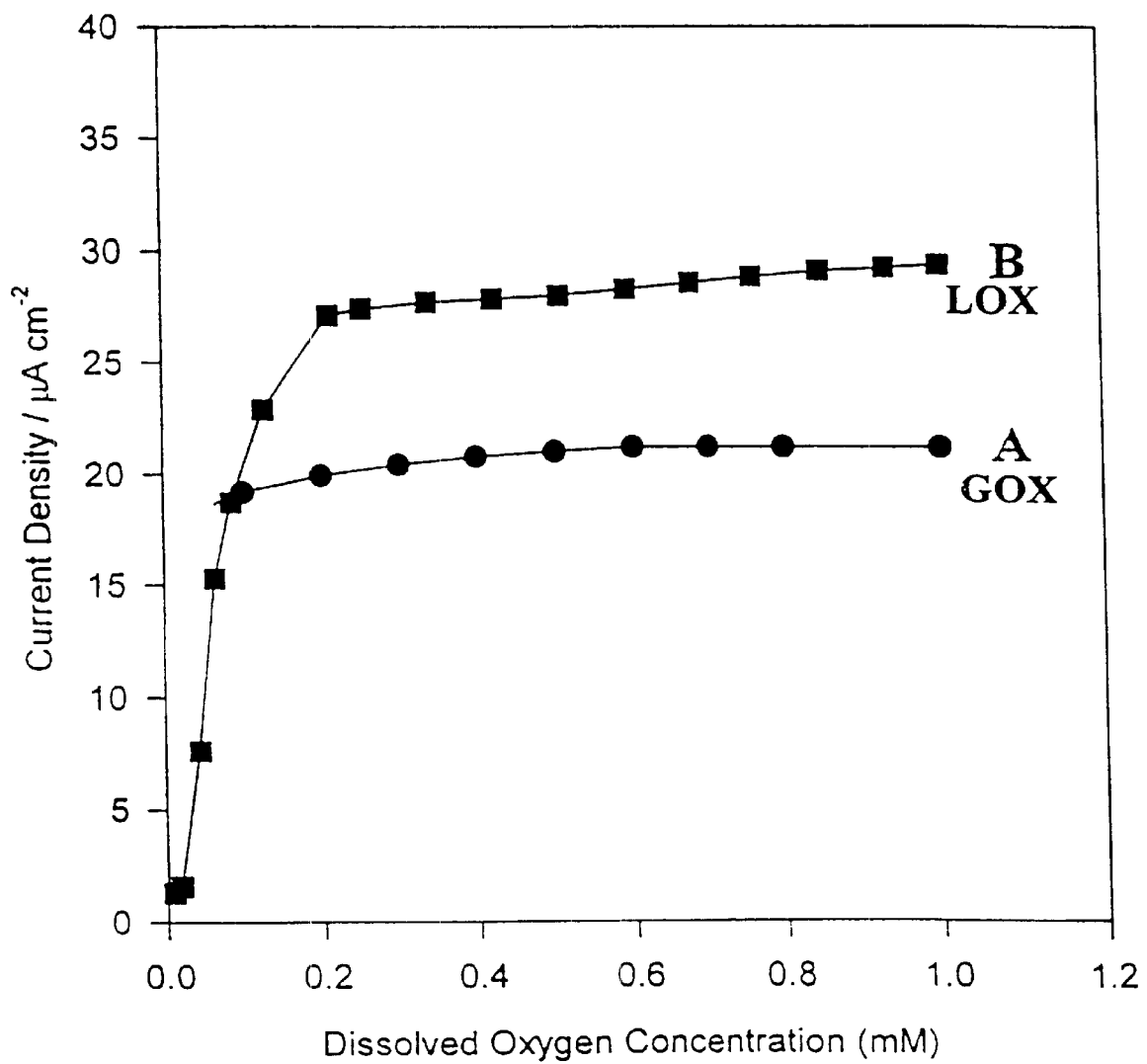
Figure 6:
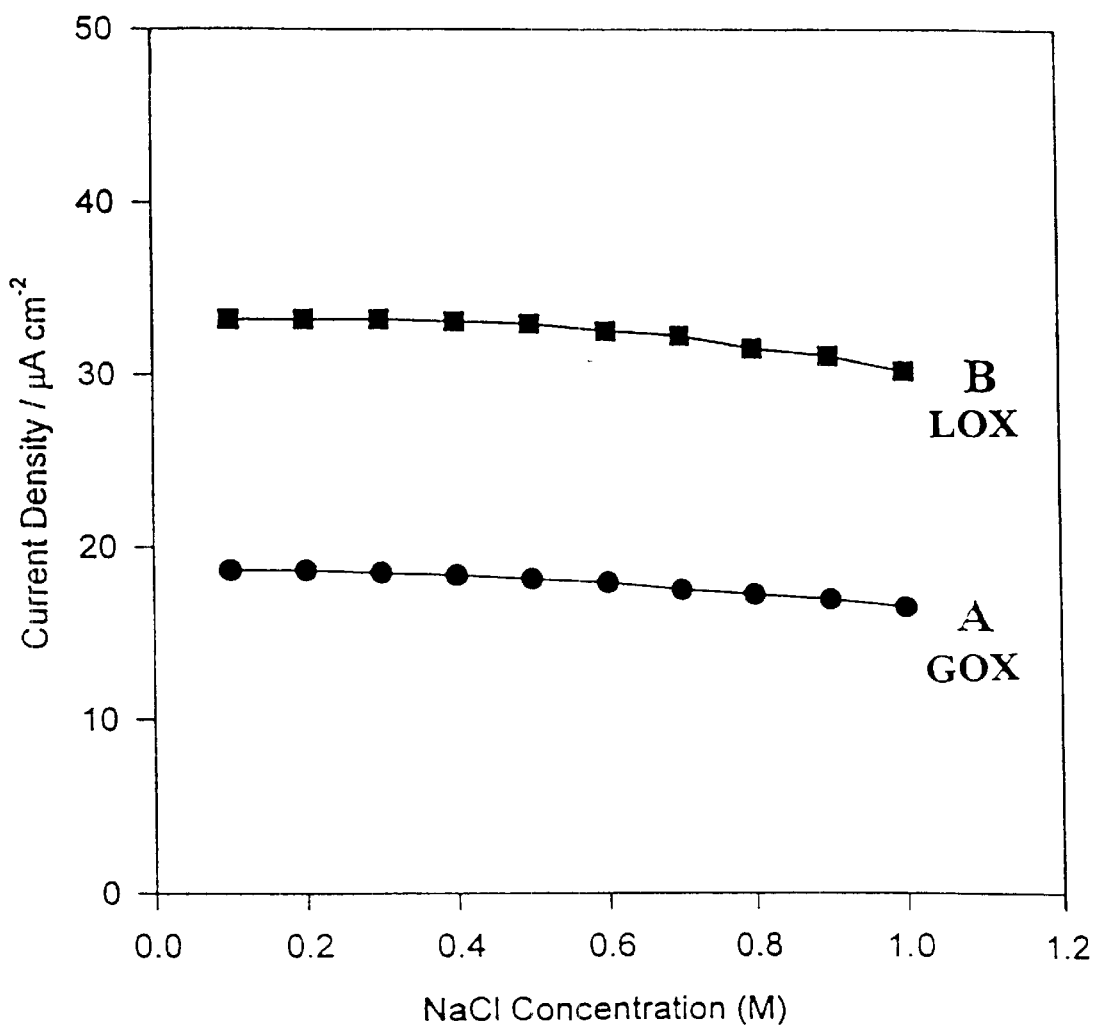
Figure 7A:
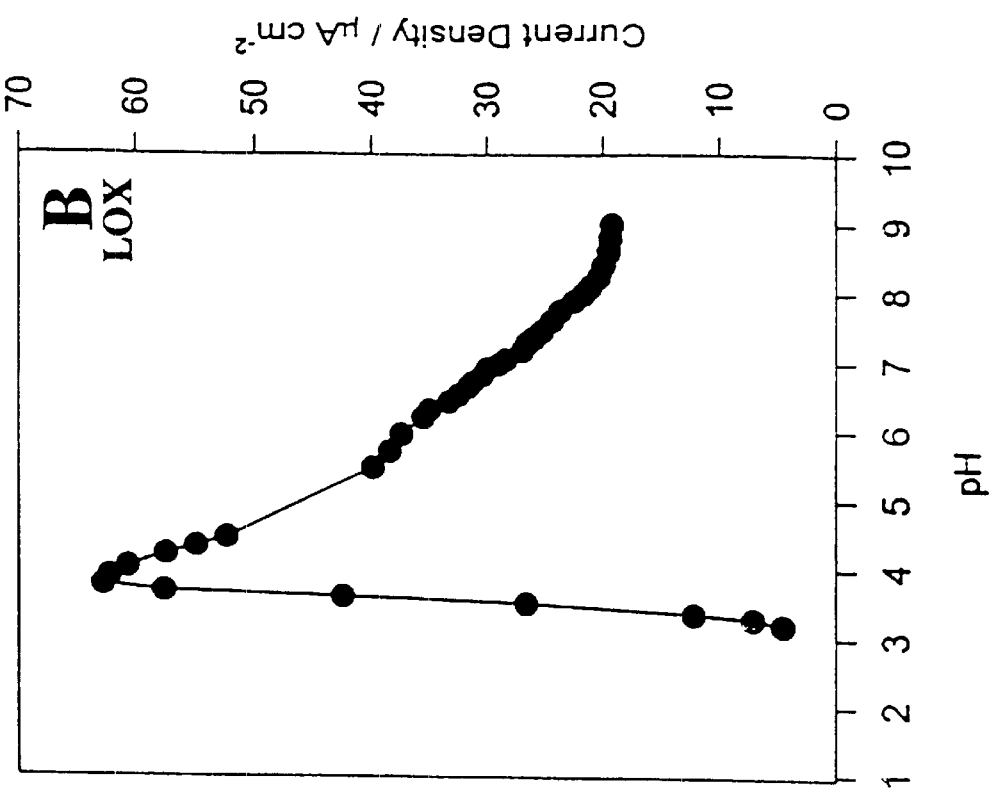
Figure 7B:
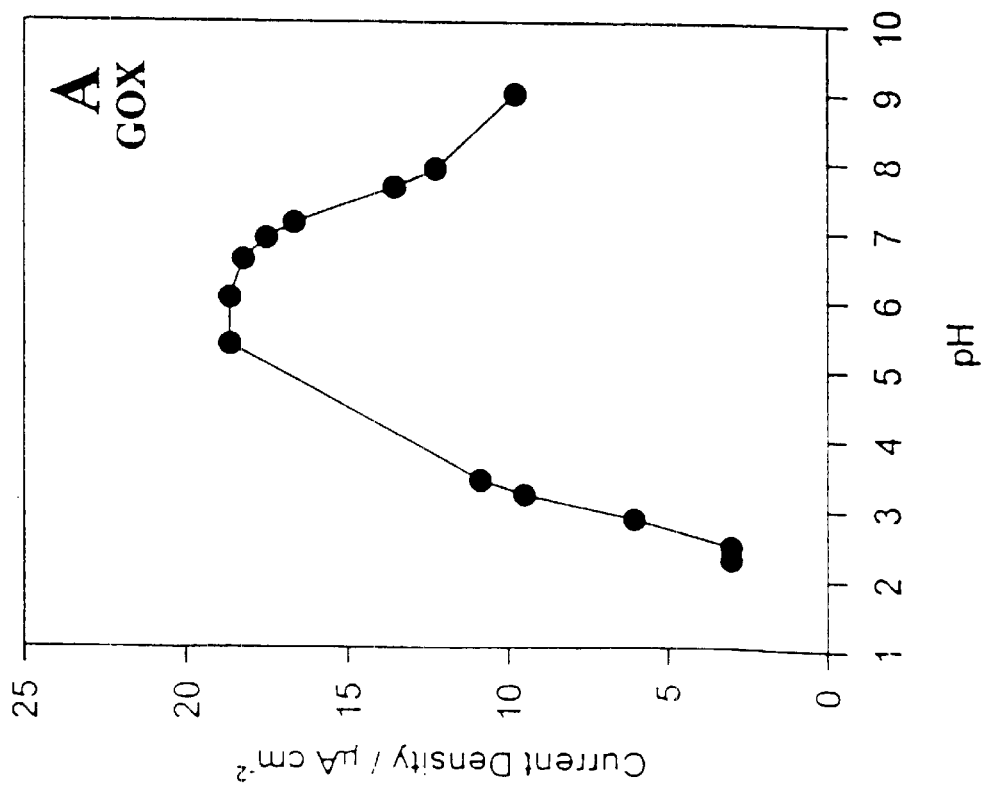
Figure 8:
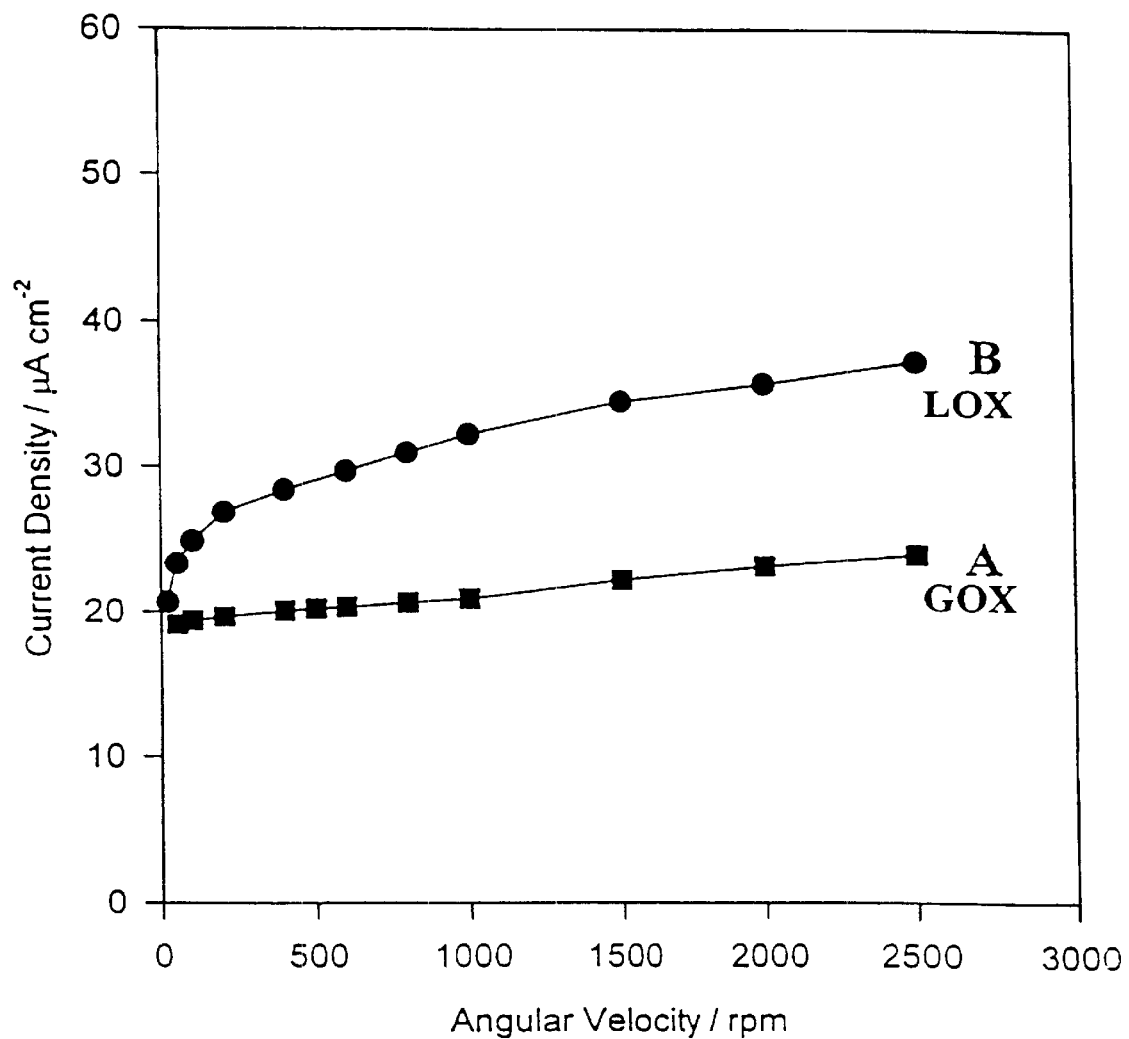
Figure 9A:
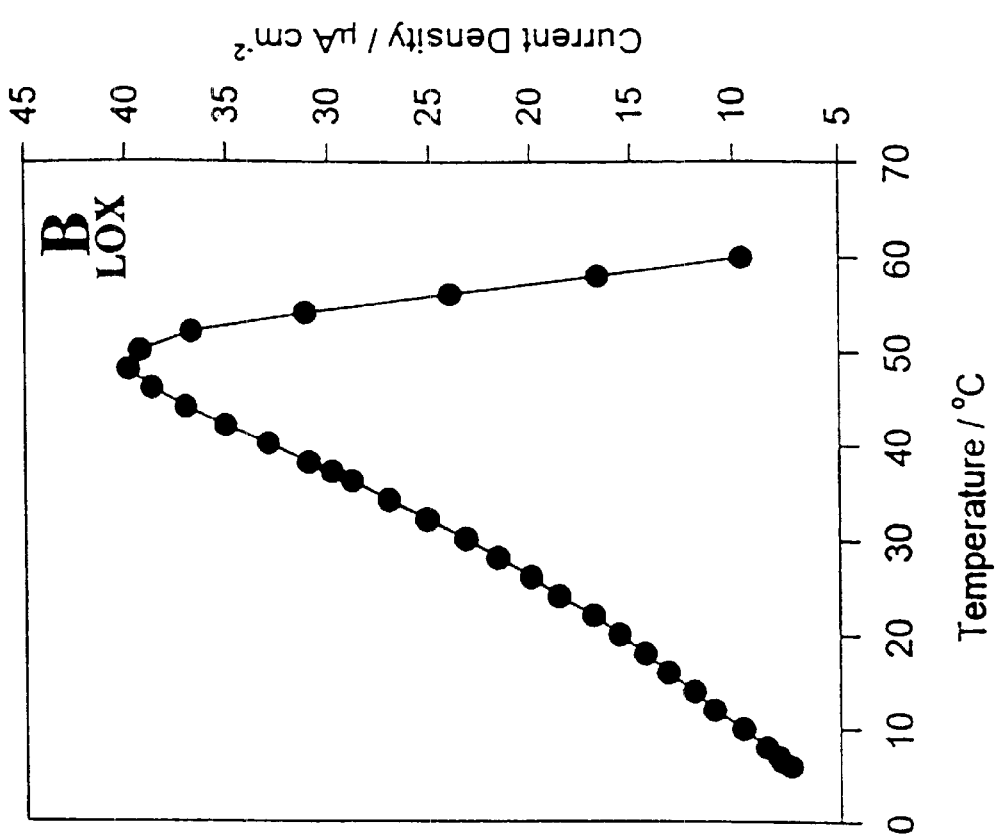
Figure 9B:
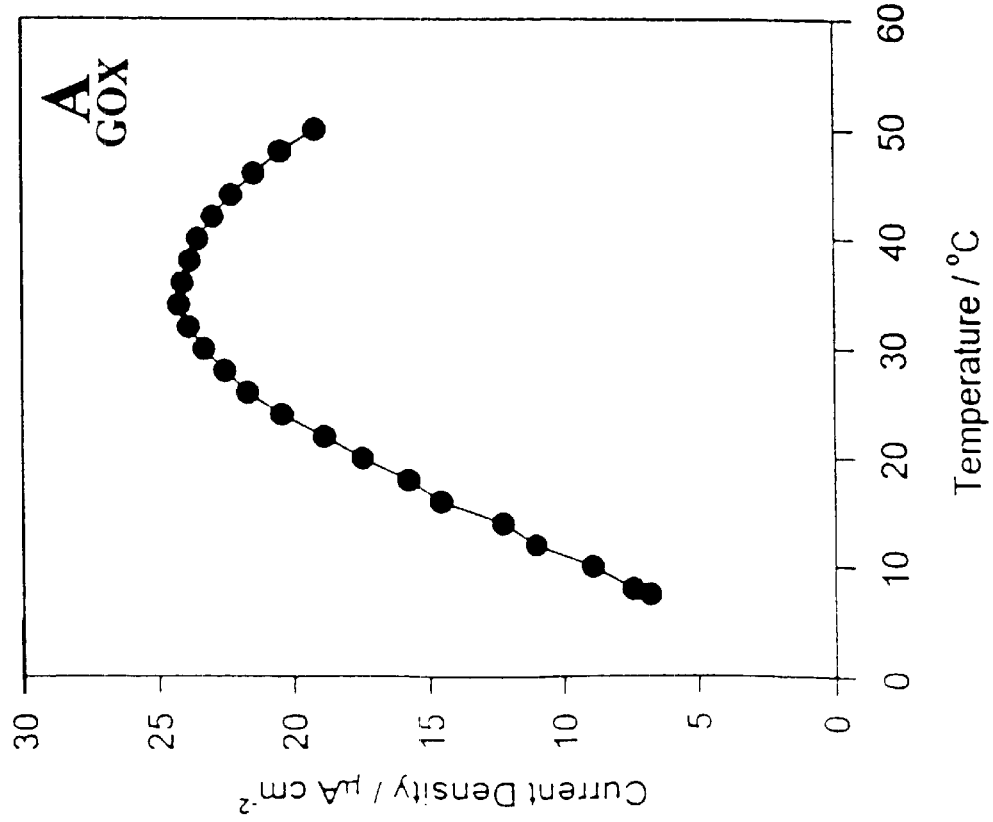

FIG. 4 is a graph showing the potential dependence of the current density for a glucose sensor according to Example 4 (5 mM glucose, 1000 rpm, 37° C., pH7.3, in air, 0.00V (SCE));

FIG. 5 is a graph showing the dependence of the current density on the dissolved oxygen concentration, according to Example 5 (1000 rpm, 37° C., pH7.3, in air, 0.00V (SCE)), (A) 5 mM glucose, (B) 5 mM lactate);

FIG. 6 is a graph showing the dependence of current density on the concentration of NaCl (1000 rpm, 37° C., pH7.3, in air, 0.00V (SCE)), (A) 5 mM glucose, (B) 5 mM lactate);

FIG. 7A and FIG. 7B are graphs showing the dependence of current density on pH,

FIG. 7A shows data for 5 mM glucose;

FIG. 7B shows data for 5 mM lactate (1000 rpm, 37° C., pH7.3, in air, 0.00V (SCE));

FIG. 8 is a graph showing the dependence of current density on the angular velocity (37° C., pH7.3, in air, 0.00V (SCE)), (A) SM glucose, (B) 5 mM lactate);

FIG. 9A and FIG. 9B are graphs showing the dependence of current density on temperature.

Figure 10A:
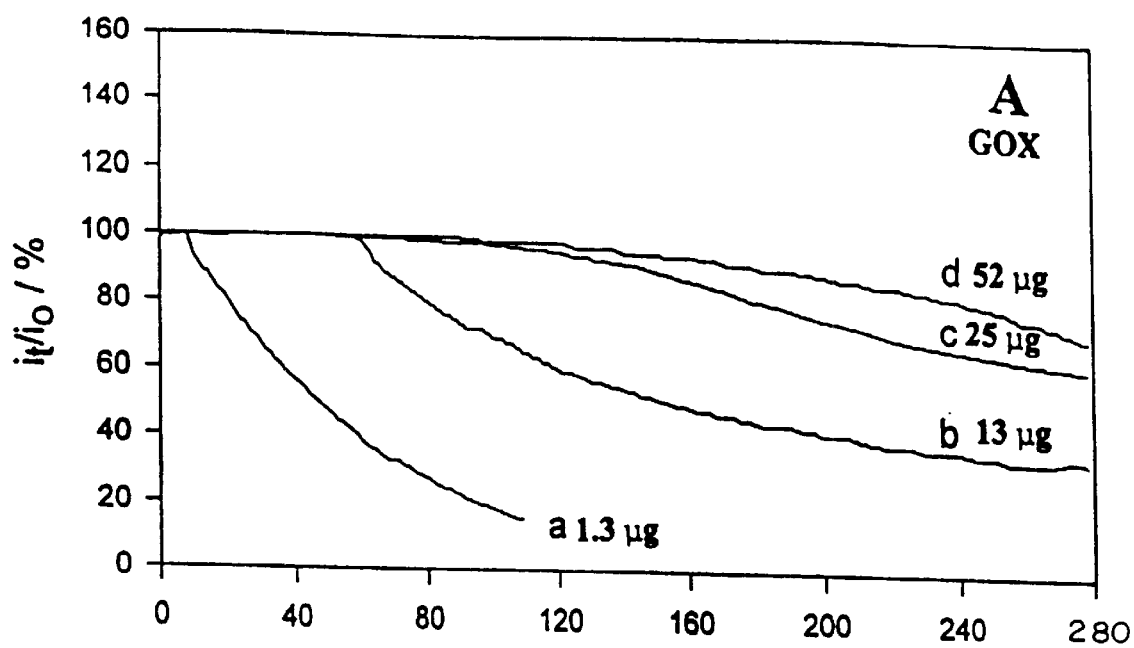
Figure 10B:
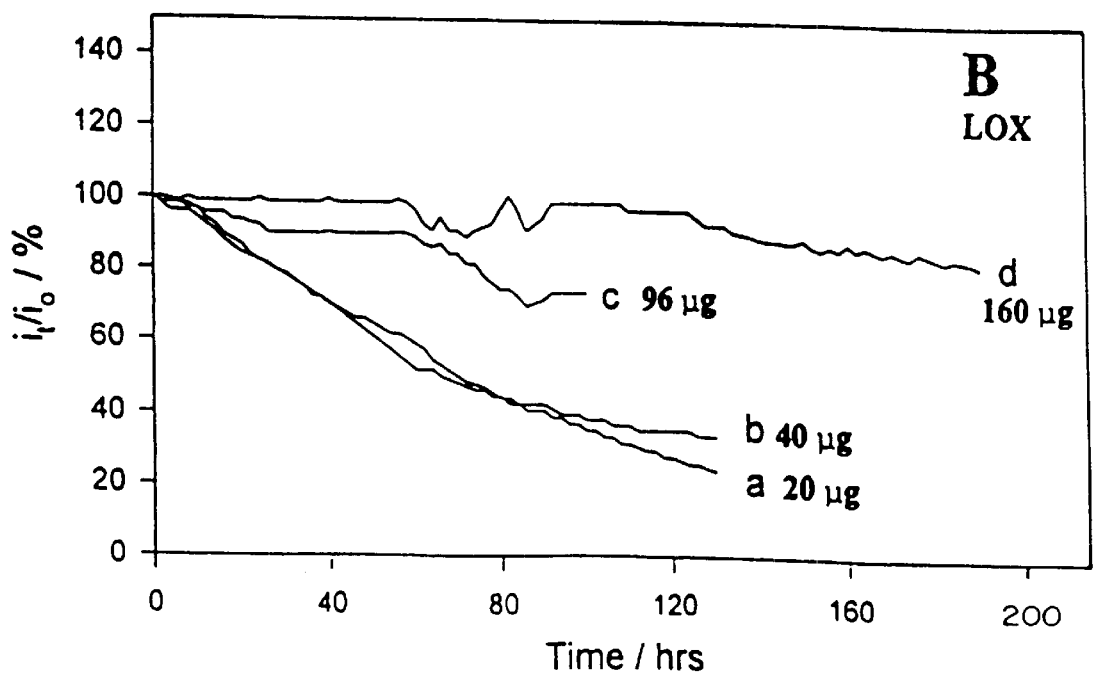
Figure 11:
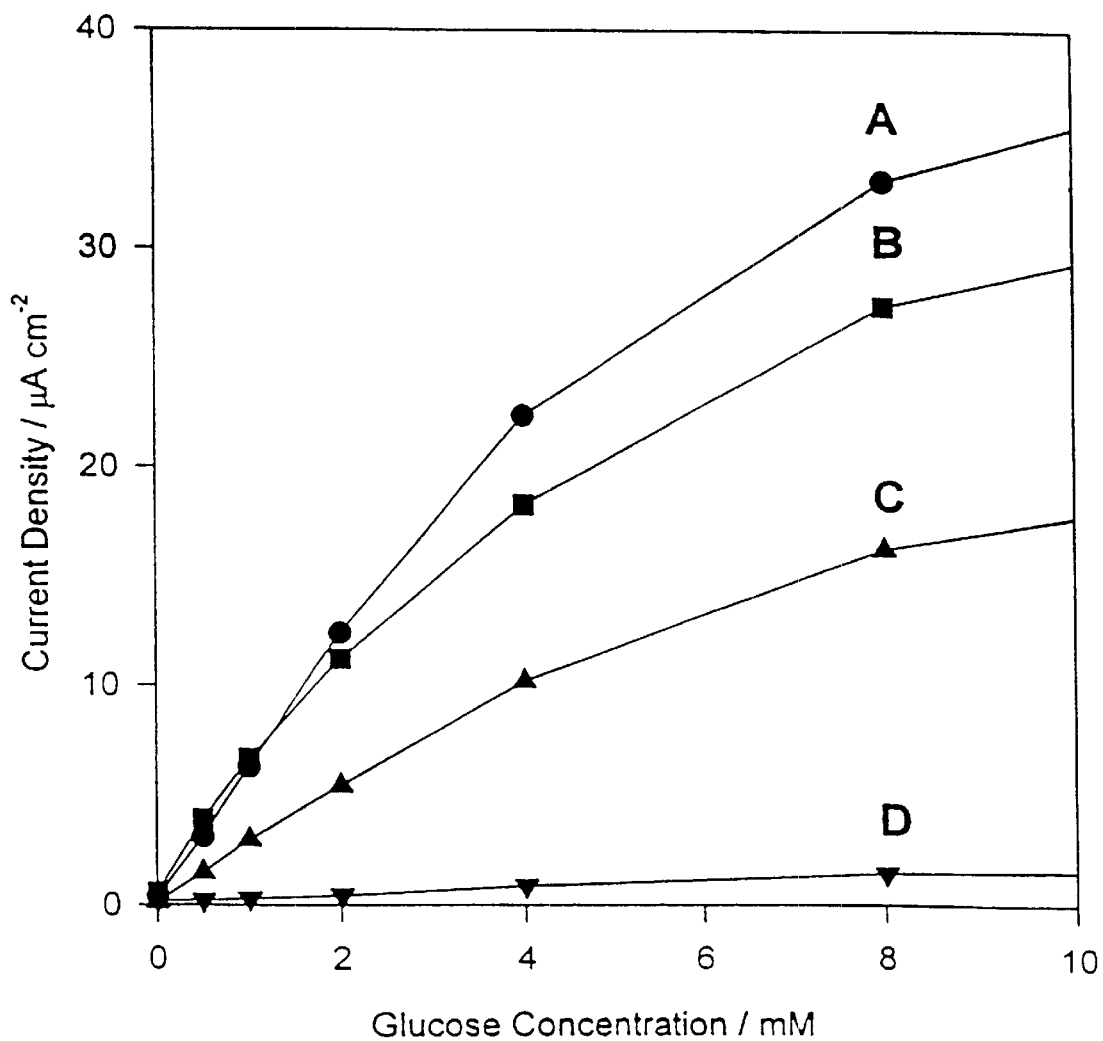
Figure 12:
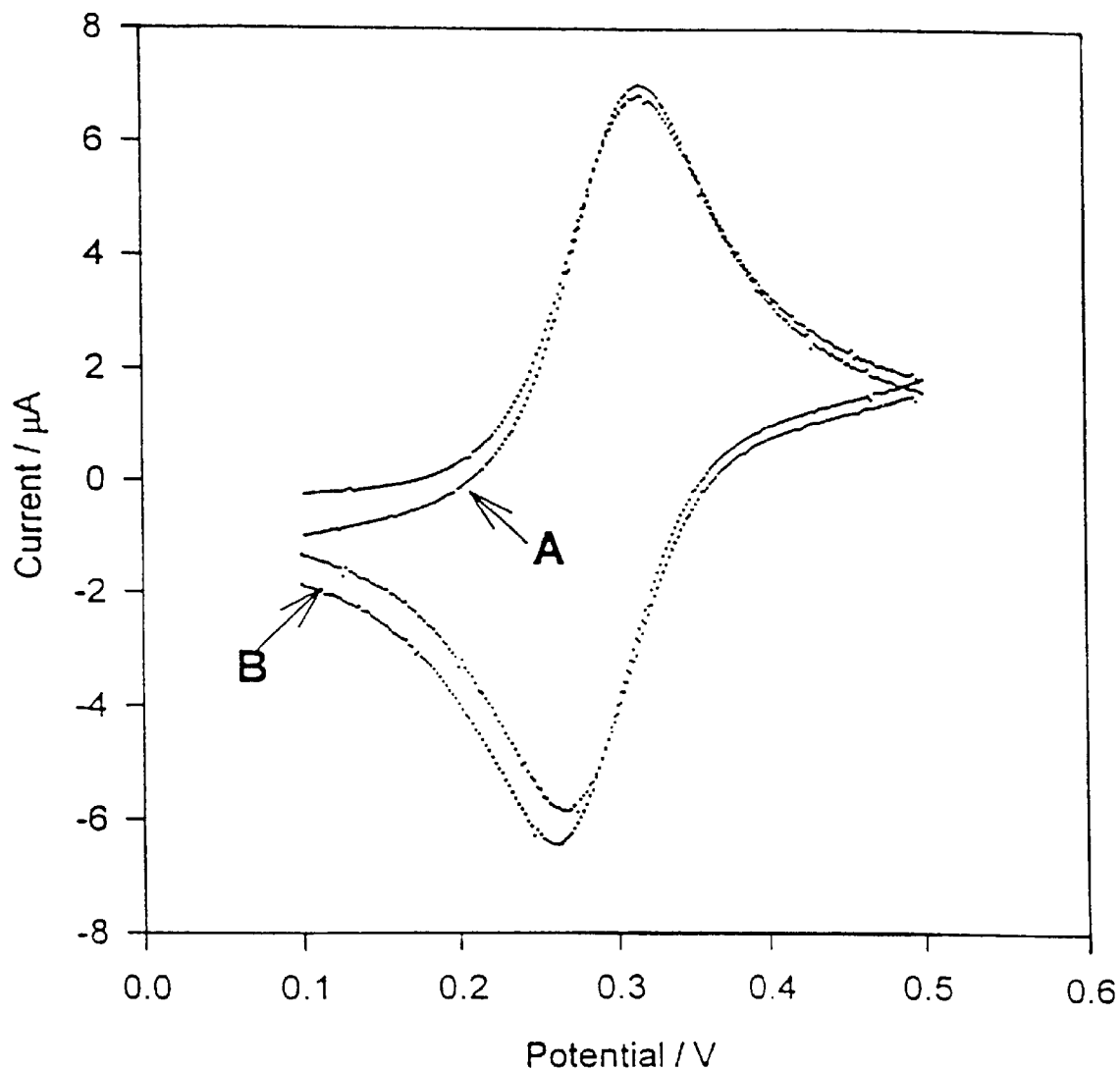
Figure 13:
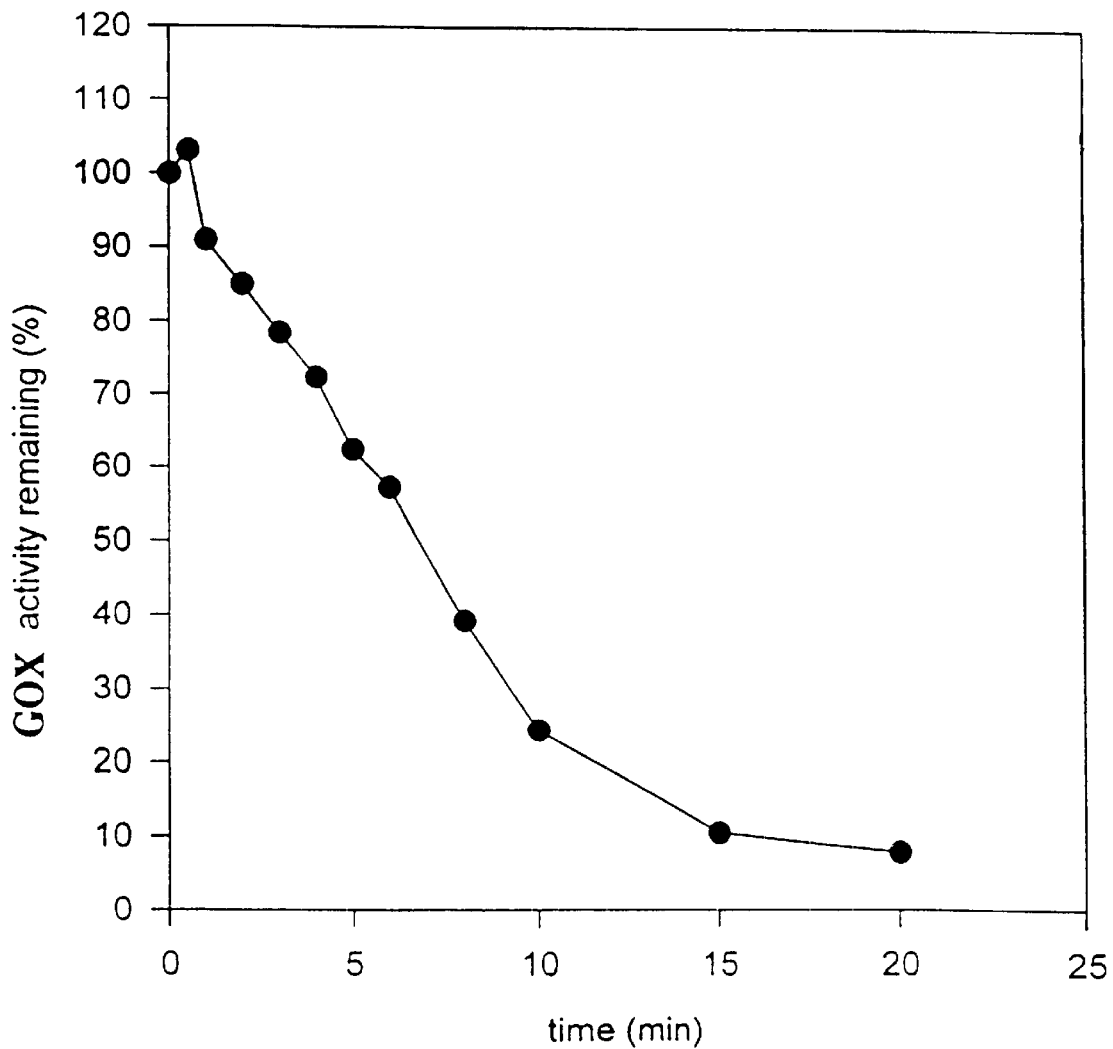
Figure 14B:
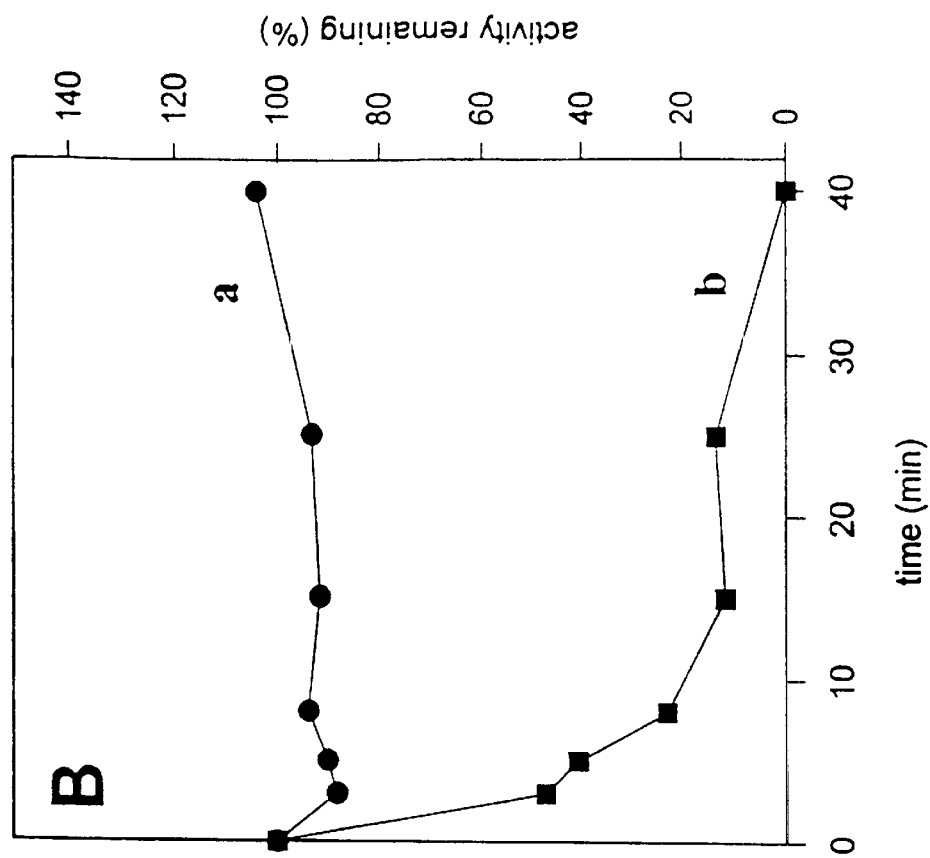
Figure 14A:
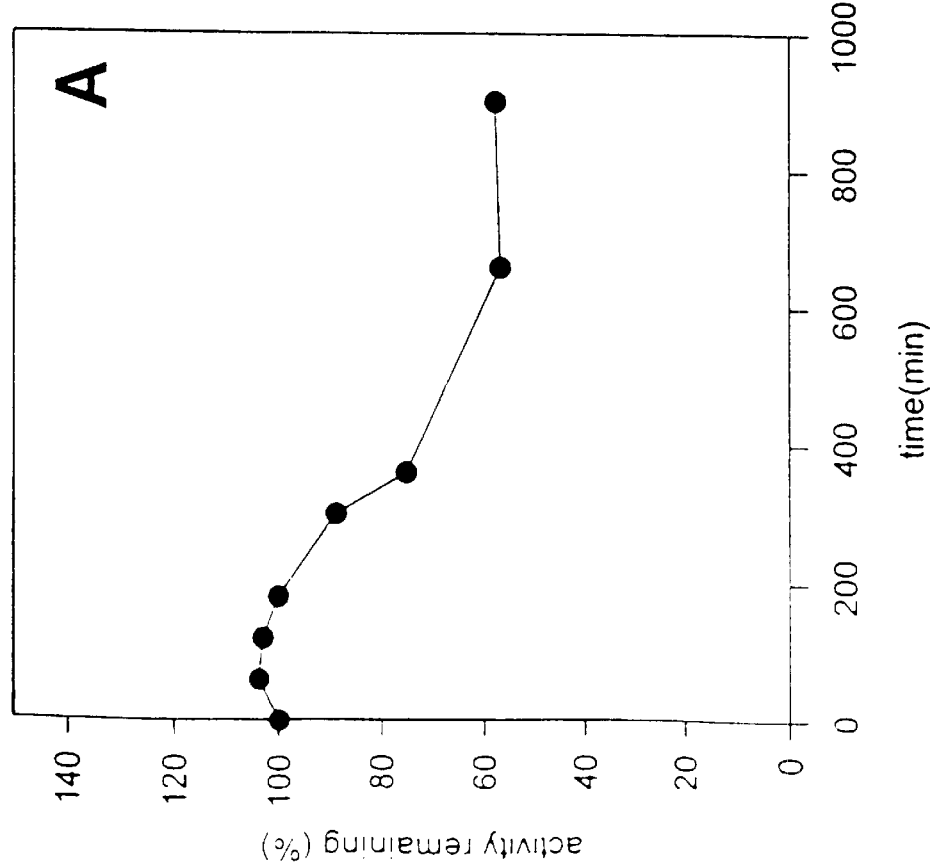
Figure 16:
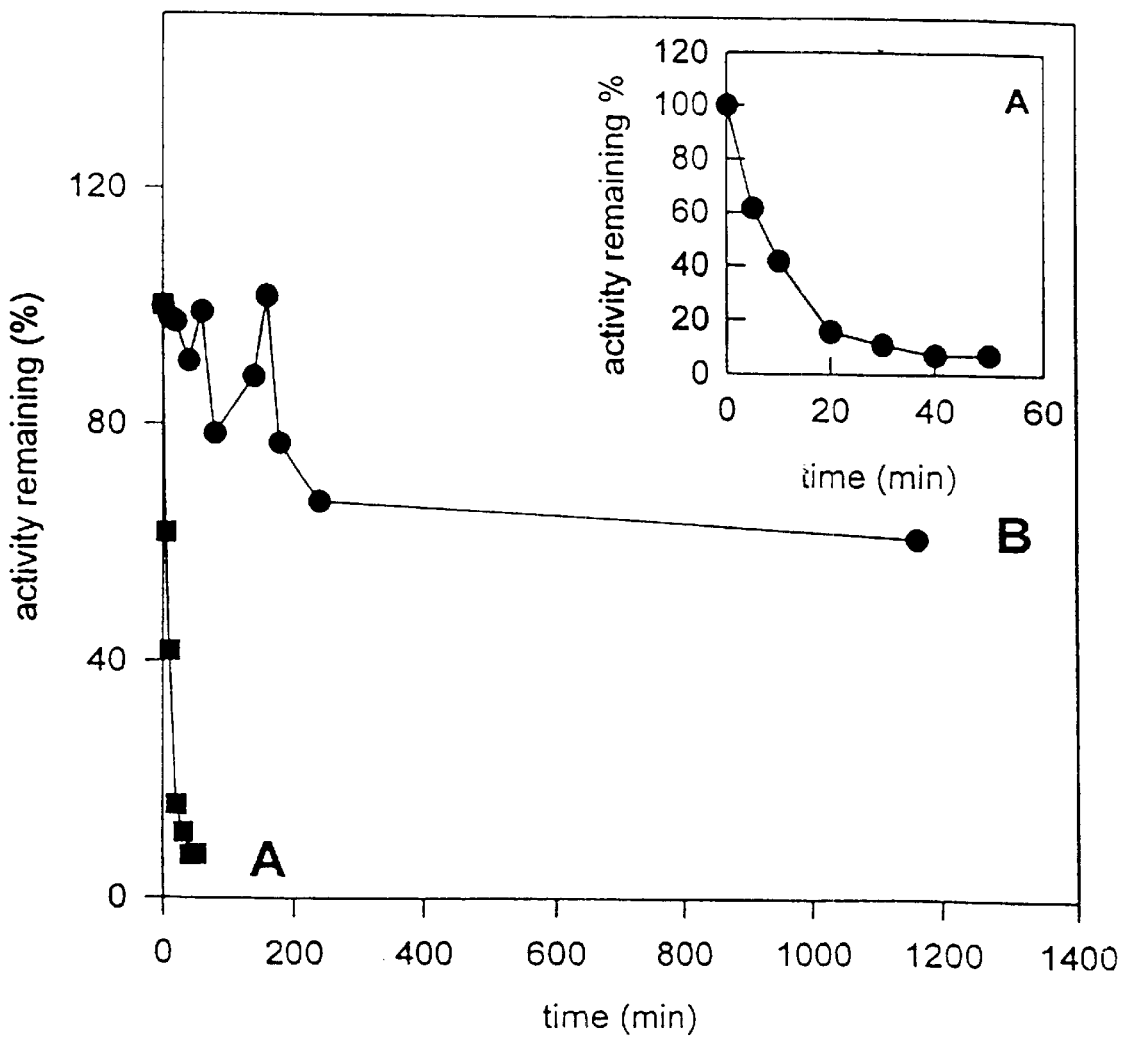
Figure 17:
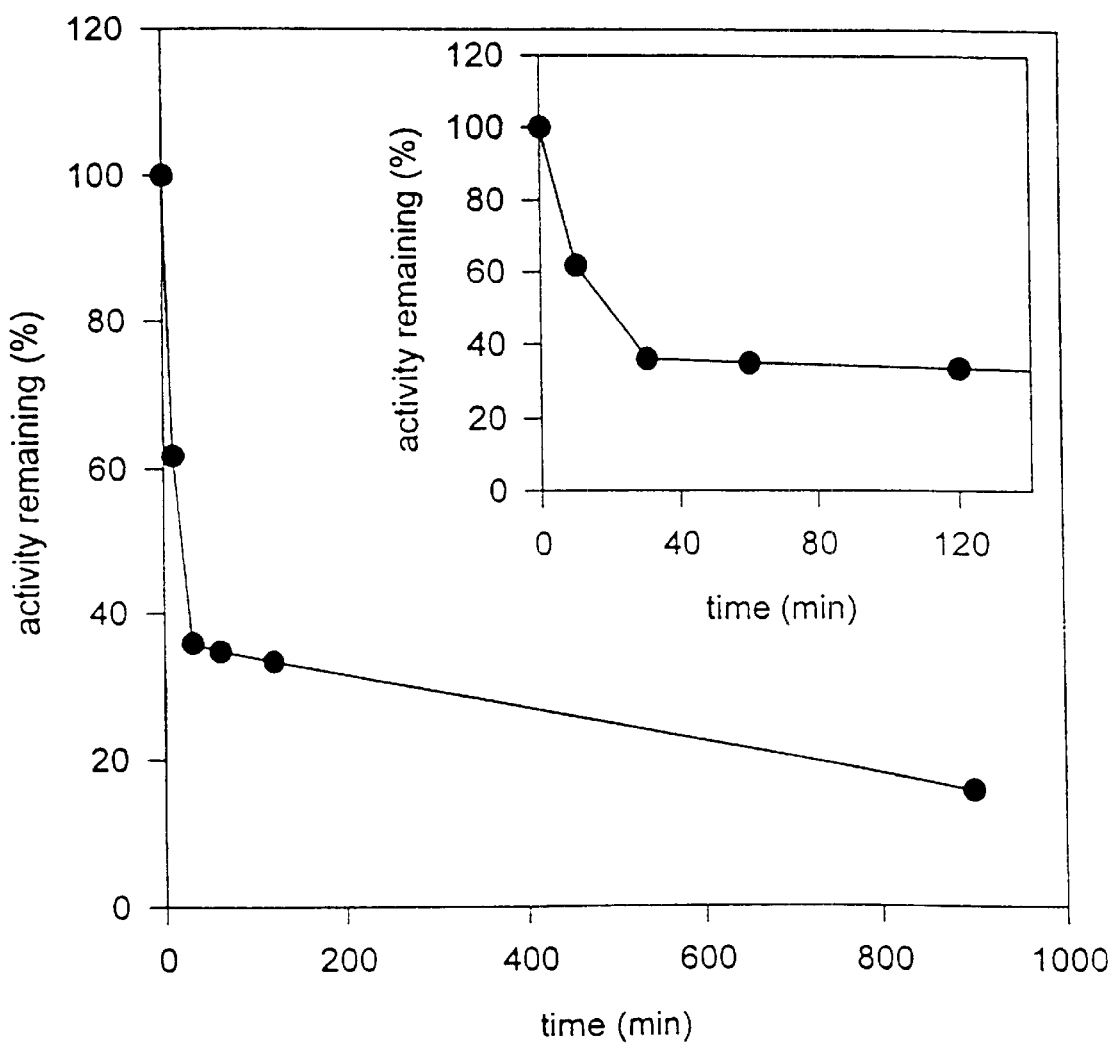
Figure 18A:
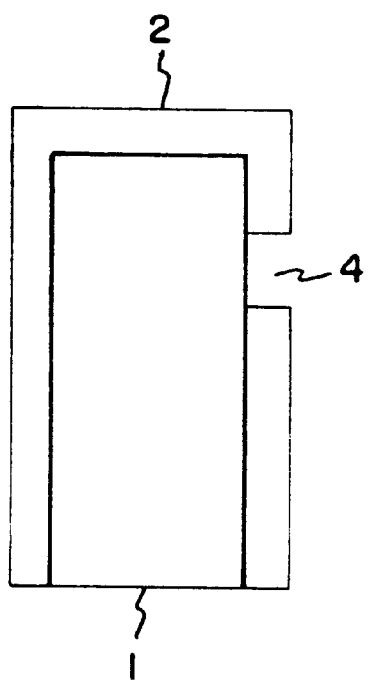
Figure 18B:
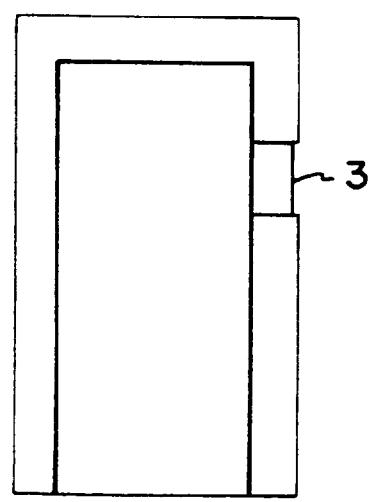

FIG. 9A shows data for 5 mM glucose;

FIG. 9B shows data for 5 mM lactate (1000 rpm, pH7.3, in air, 0.00V (SCE));

FIG. 10A and FIG. 10B are graphs showing the stability of thermostable peroxidase-based glucose and lactate sensors at different oxidase loadings: Figure (a) 1.3 $\mu$g; (b) 13 $\mu$g; (c) 26 $\mu$g; (d) 52 $\mu$g of immobilized glucose oxidase (FIG. 10A); (a) 20 $\mu$g; (b) 40 $\mu$g; (c) 96 $\mu$g; (d) 160 $\mu$g of immobilized lactate oxidase (FIG. 10B) (1000 rpm, 37° C., pH7.3, in air, 0.00V (SCE));

FIG. 11 is a graph showing glucose calibration curves before and after 280 hours of operation at 37° C. in the stability study of Example 8, (A) 26 $\mu$g GOx before stability experiment; (B) 26 $\mu$g GOx after stability experiment; (C) 1.3 $\mu$g GOx before stability experiment; (D) 1.3 $\mu$g GOx after stability experiment (1000 rpm, 37° C. pH7.3, in air, 0.00V (SCE));

FIG. 12 is a graph showing cyclic voltammograms of the glucose sensor before and after 280 hours of operation at 37° C.; (A) after stability experiment; (B) before stability experiment;

FIG. 13 is a graph of the time dependence of lactate oxidase activity in solution at 63° C.;

FIG. 14A and FIG. 14B are graphs showing time dependence of lactate oxidase-doped silica gel powder activity at 63° C.; FIGS. 14A and 14B(a): PVI-lactate oxidase-doped silica gel, FIG. 14B(b): lactate oxidase-doped silica gel;

FIG. 15 is a graph showing time dependence of the activity of lactate oxidase in different environments at 50° C., (A) PVI-LOx-doped silica gel; (B) Lox-doped silica gel; (C) PVI-LOx in solution; (D) LOx in solution;

FIG. 16 is a graph showing time dependence of the activity of glucose oxidase in different environments at 63° C. (A), glucose oxidase in solution; (B) glucose oxidase-doped silica gel powder; the inset shows the short term behavior of (A);

FIG. 17 is a graph showing time dependence of PEI-lactate oxidase-doped silica gel powder activity at 63° C., inset shows the short term behavior;

FIG. 18A is a diagrammatic representation of an electrode;

FIG. 18B is a diagrammatic representation of an electrode with a sensing layer.

Figure 19:
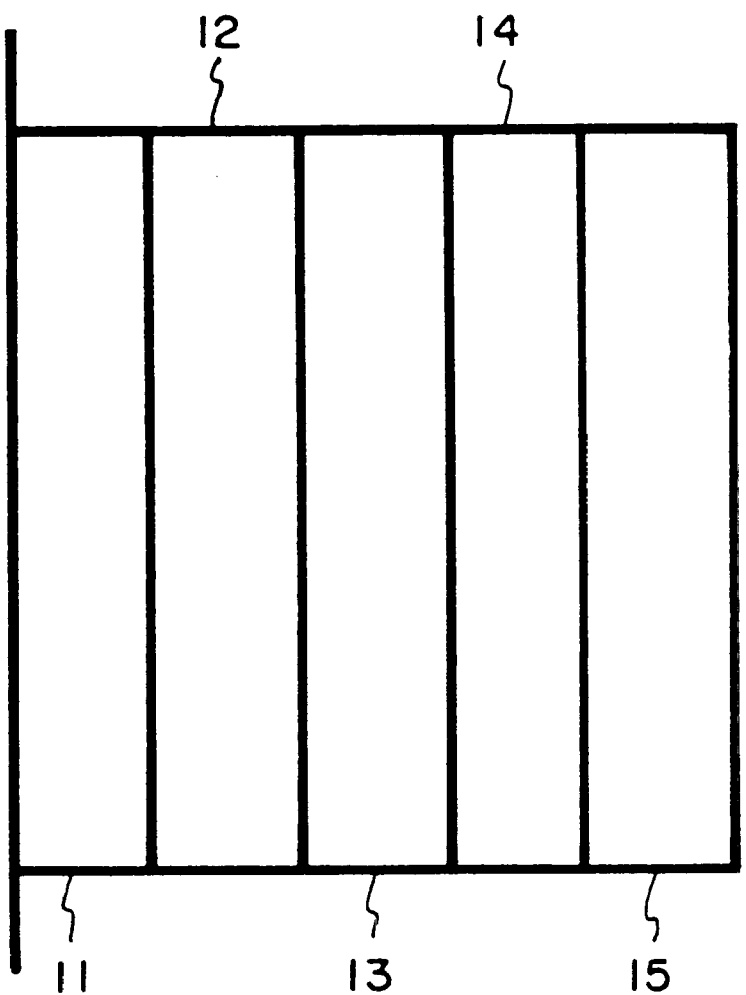
Figure 20:
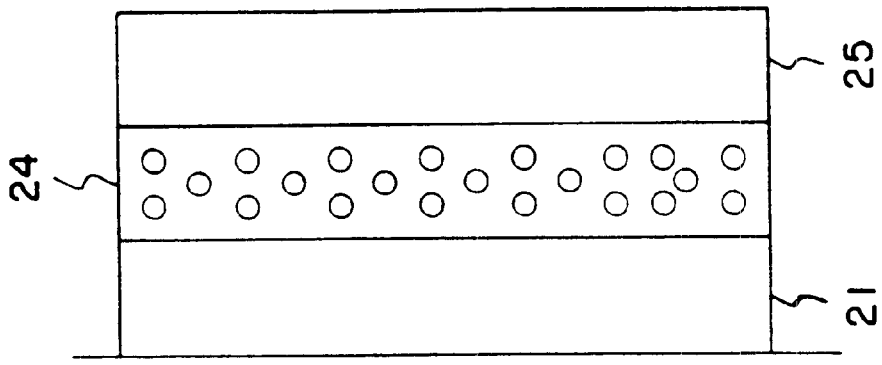
Figure 21:
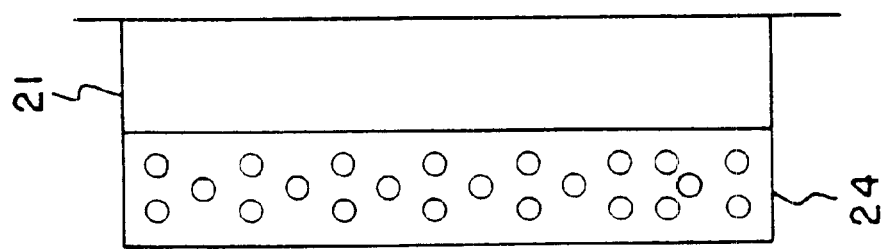

FIG. 19 is a diagrammatic representation of a sensing layer of a biosensor of the invention;

FIG. 20 is a diagrammatic representation of a two-layered sensing layer of a thermostable biosensor of the invention; and FIG. 21 is a diagrammatic representation of a three-layered sensing layer of a thermostable biosensors of the invention.

DETAILED DESCRIPTION OF THE INVENTION

Referring to the drawings in general and FIGS. 18(a)–(b) in particular, the sensors of the invention typically include a non-corroding working electrode 1 which is substantially covered by an insulator 2 having a recess 4 to allow electrolytic contact between an analyte-containing fluid and the working electrode 1. A film 3, having a plurality of layers, is positioned within recess 4. FIGS. 19–21 show three embodiments of film 3. In general, film 3 includes a sensing layer 11, 21 and a second enzyme layer 13, 24. Film 3 may also contain one or more optional layers, such as an electrically insulating layer 12 between the sensing layer 11 and second enzyme layer 13; an analyte-transport controlling layer 14 to control the flow of analyte to the sensing layer 11; and a biocompatible layer 15, 25 for biocompatiblity of the sensor in body fluids.

Electrodes

The electrochemical sensors of the invention include at least two electrodes for contacting the electrolytic solution to be assayed. One of these electrodes is a working electrode 1, which is made from non-corroding metal or carbon. A carbon working electrode may be vitreous or graphitic and can be made from a solid or a paste. A metallic working electrode may be made from platinum group metals, including palladium or gold, or a non-corroding metalically conducting oxide, such as ruthenium dioxide. The working electrode may be a wire or a thin conducting film applied to a substrate, for example, by coating or printing.

Typically, only a portion of the surface of the metallic or carbon conductor is in electrolytic contact with the analyte-containing solution. This portion is called the working surface of the electrode. The remaining surface of the electrode is isolated from the solution by an insulator 2. Examples of useful insulators include polymers such as polyimides, polytetrafluoroethylene, polyhexafluoropropylene and silicones, also known as polysiloxanes.

In addition to the working electrode, the sensors of the invention also include a reference electrode or a combined reference and counter electrode (also termed a quasi-reference electrode or a counter/reference electrode). The reference or counter/reference electrode may be, for example, a silver/silver chloride electrode. If the sensor does not have a counter/reference electrode then it will include a separate counter electrode, which may be made from the same materials as the working electrode.

Sensors of the present invention have one or more working electrodes and one or more counter, reference, and/or counter/reference electrodes. One embodiment of the sensor of the present invention has two or more working electrodes. These working electrodes may be integrally connected or they may be kept separate.

Typically, for in vivo use the working electrodes of the present invention are implanted subcutaneously in the skin of a patient for direct contact with the body fluids of the patient, such as blood. When multiple working electrodes are used, they may be implanted together or at different positions in the body. The counter, reference, and/or counter/reference electrodes may also be implanted either proximate to the working electrodes or at other positions within the body of the patient. Alternatively, the counter, reference, and/or counter/reference electrodes may be placed on the skin of the patient.

Sensing Layer

The portion of the working electrode that is not insulated is coated with a sensing layer 3. The typical sensing layer 3 of the sensors of the present invention includes a redox polymer which is capable of swelling in water to form a redox hydrogel. Sensing layer 3 also typically includes an enzyme which is capable of catalyzing a reaction of the analyte or an analyte-generated compound. Preferably, that enzyme is immobilized in the redox polymer. In one embodiment of the invention, the sensor contains a peroxidase which is preferably a thermostable peroxidase such as soybean peroxidase. The peroxidase-containing hydrogel forms a sensing layer that transduces a flux of $H_2O_2$ into an electrical signal.

The redox polymer contains redox centers that are bound to the polymer by covalent, coordinative, or electrostatic bonds; the latter resulting preferably from interactions of charged sites of the polymer with an oppositely charged redox species. Preferably, the redox mediator is covalently or coordinatively bound to the redox polymer, although it may also be immobilized by entrapment or by electrostatic bonding.

The redox centers are preferably non-leachable. For redox species electostatically bound to the polymer, the absence of leaching generally requires that the charged redox species has, at the pH of the analyte solution, a charge of at least two, and preferably three or more. For example, if the redox species is a cation, it preferably has at least a +2 charge, and is preferably +3 or better. The greater the charge of the redox species, the slower the leaching. Similarly, if the redox species is an anion and the binding to the polymer is electrostatic, then it should have a -2 charge and is preferably -3 or better. Preferably, most of the redox centers (at least about 90%) remain electrode-bound for at least 14 days at 37° C.

The redox polymer is designed to swell in water and dilute aqueous solutions. The water uptake should add at least 10 weight percent, and preferably 20 weight percent, to the weight of the dry polymer. The thermostable peroxidase in the redox polymer layer is not substantially leached by water or by a physiological buffer solution at 37° C. The redox polymer layer containing the thermostable peroxidase can be conveniently made, for example, as described by Gregg and Heller, *J. Phys. Chem.* 95:5970 (1991), in U.S. Pat. No. 5,262,035, and in copending U.S. patent application Ser. No. 08/540,789, filed Oct. 11, 1995.

In general, the redox polymer contains redox centers that are stable and have a redox potential between about -0.1 V (vs SCE) and about +0.6V (vs SCE). The preferred range is between about -0.1V (vs SCE) and about +0.4V (vs SCE). Poising the electrode at a potential where $O_2$ is not electroreduced is desirable; otherwise the measured signal resulting from the electroreduction of $H_2O_2$ to water must be corrected for the background caused by electroreduction of dissolved $O_2$. Furthermore, it is also desirable to poise the electrode at a potential where the rate of electrooxidation of other interferants, such as urate, ascorbate, and acetaminophen, is not significant, so that correction for their electrooxidation will not be required.

Examples of useful redox centers that can be bound to the polymer of the sensing layer are described in U.S. Pat. Nos. 5,264,104; 5,356,786; 5,262,035; and 5,320,725, herein incorporated by reference. Typically, the redox mediators are metal complexes, particularly of osmium, ruthenium, iron and cobalt, or organic redox compounds, such as quinones and other compounds having a quinoid structure. The preferred redox centers exchange electrons rapidly with each other. One example of the preferred redox centers are osmium transition metal complexes with one or more ligands having a nitrogen-containing heterocycle such as 2,2'-bipyridine, 1,10-phenanthroline or derivatives thereof. In particular, it has been determined that osmium cations complexed with two ligands containing 2,2'-bipyridine, 1,10-phenanthroline, or derivatives thereof, the two ligands not necessarily being the same, form particularly useful redox centers in the sensors of the present invention. Preferred derivatives of 2,2'-bipyridine for complex formation with the osmium cation are 4,4'-dimethyl-2,2'-bipyridine and mono-, di-, and polyalkoxy-2,2'-bipyridines such as 4,4'-dimethoxy-2,2'-bipyridine, where the carbon to oxygen ratio of the alkoxy groups is sufficient to retain solubility of the transition metal complex in water.

One useful group of redox polymers is derived from poly(4-vinyl pyridine) and is made by complexing between one third and one fifteenth of the pyridine rings with $[Os(bpy)_2Cl]^{+/2+}$ where bpy is 2,2'-bipyridine, or with $[Os(phen)_2Cl]^{+/2+}$ where phen is 1,10-phenanthroline, and where, preferably, some of the pyridine rings of the polymer are quaternized by reaction with 2-bromoethylamine. Useful polymers are also derived from poly-(N-vinyl imidazole) (termed PVI), poly(acrylamide co-4-vinylpyridine), and poly(acrylamide co-4-vinylimidazole).

To produce the inventive sensors, a hydrogen peroxide sensing layer, containing a thermostable peroxidase, is prepared by the dropwise mixing of solutions of the peroxidase, the redox polymer, and a crosslinker on a clean electrode surface. These solutions are allowed to dry and cure. The solutions may also be premixed, and a droplet of the premixed solution may be placed on the electrode. An example of a useful crosslinker is poly(ethylene glycol) diglycidyl ether with a molecular weight between 300 and 600, preferably 400 and 600. Another useful crosslinker is the bis N-hydroxysuccinimide ester of poly(ethylene glycol)-α,ω-dicarboxylic acid.

Second Enzyme Layer

A second enzyme layer 13 on the working electrode catalyzes the reaction of $O_2$ with a substrate whereby $H_2O_2$ is produced. The substrate is generally the analyte to be assayed by the sensor. Alternatively, the substrate is a reaction product of the analyte to be assayed, for example the product of hydrolysis of the analyte. The second enzyme used in layer 13 is also termed herein the peroxide-generating enzyme. In the inventive sensors, the redox centers of the peroxide-generating enzyme are prevented from being reduced or oxidized directly by electron exchange with the redox polymer of the sensing layer. Prevention of such oxidation or reduction is accomplished by methods discussed hereinbelow.

First, prevention of oxidation/reduction of the peroxide-generating (second) enzyme by the redox polymer can be intrinsic to the second enzyme. For example, the second enzyme may include a sufficiently thick, natural, electrically insulating protein or glycoprotein layer over its reaction center or centers. Such a layer prevents electron transfer to or from the redox polymer. In this case, no further means for preventing reduction or oxidation of the second enzyme by the redox polymer is required.

Inorganic Polymeric Matrix Immobilization and Stabilization

Alternatively, the $H_2O_2$-generating (second) enzyme is immobilized in a non-conducting inorganic or organic polymeric matrix to prevent electron exchange between its redox centers and the redox polymer. The immobilizing matrix is preferably highly permeable to $O_2$ and usually is more permeable to $O_2$ than to the analyte or to its precursor. The preferred immobilizing matrices are those in which the second enzyme is stabilized, becoming itself thermostable through immobilization, as discussed more fully below.

The sol-gel polymerization process provides a method for the preparation of an inorganic polymeric matrix (e.g., glass) by the polymerization of suitable monomers at or near room-temperature. Suitable monomers include alkoxides and esters of metal and semiconducting elements, with preferred metals and semiconductors comprising Si, Al, Ti, and Pb. The most preferred monomers include silicon and have a silicon to oxygen ratio of between about 1:2 and about 1:4.

Enzymes can be immobilized in silica and other inorganic polymeric matrices made by sol-gel processes, involving, for example, the hydrolysis of tetramethoxysilane or another polyalkoxysilane that may contain one or more silicon atoms. Condensation of the resulting silanol in the presence of the enzyme results in entrapment of the enzyme. This process has been referred to as sol-gel immobilization.

Enzymes can be immobilized in inorganic polymeric matrices to prevent electrical contact between the immobilized second enzyme and the redox polymer and/or electrode. Furthermore, binding of enzymes in silica or other inorganic polymeric matrices formed from sol-gels can stabilize the enzyme. Entrapment of glucose oxidase, a glycoprotein, in silica sol-gel greatly improves the stability of the enzyme, which retains activity when heated in water to 98° C. for 10 minutes.

When lactate oxidase, which is not a glycoprotein, was similarly immobilized by the sol-gel process in silica, the enzyme was not particularly thermostable. However, when lactate oxidase is dissolved in an aqueous buffer solution in which poly(N-vinyl imidazole) is co-dissolved, and the lactate oxidase-poly(N-vinyl imidazole) mixture is immobilized in the silica by the sol-gel process, a uniquely stable, immobilized lactate oxidase is obtained. The stabilized lactate oxidase can be heated in water to 90° C for 10 minutes and still retain enzymatic activity.

Poly(N-vinyl imidazole), a polycation at pH 7, binds at this pH to enzymes such as lactate oxidase, that are polyanions at pH 7. Thus, the addition of a particular polymer to a particular enzyme can greatly increase the stability the enzyme. In the case of lactate oxidase, addition of polyethyleneimine, also a polybasic polymer and also multiply protonated at pH 7, in place of poly(N-vinyl imidazole) improved stability of the enzyme, although not as much as the addition of the preferred polymer, poly(N-vinyl imidazole).

If the enzyme is a polycation or polyanion at a particular pH, a polymeric polyanion or polycation, respectively, can be coimmobilized in an inorganic polymeric matrix formed from a sol-gel to stabilize the enzyme. The stabilized enzyme can then be used at higher temperatures and/or for longer durations than would be possible if the enzyme were immobilized alone in the sol-gel.

After gelling, the silicas, in which the peroxide-generating, now thermostable, second enzyme is immobilized, are hard materials that can be ground into fine powders. These powders are then dispersed in highly $O_2$-permeable polymers, further discussed hereinbelow, to form a peroxide-generating second layer 13 of the inventive sensors. The peroxide-generating layer 13 preferably has the following desired properties: thermostability; absence of electron transfer between the redox polymer of the sensing layer and the redox centers of the enzyme of the second enzyme containing $H_2O_2$-generating layer, i.e. absence of oxidation or reduction of the redox polymer by redox centers of the second enzyme; and high $O_2$ permeability.

Alternatively, when electron transport between the redox polymer of the sensing layer and the peroxide-generating second enzyme is avoided because of intrinsic electrical insulation of the $H_2O_2$ generating enzyme or by immobilization of the enzyme in an electrically insulating matrix (such as the inorganic polymeric matrices described above), it is practical to incorporate the second enzyme in the peroxidase-containing sensing layer. In this case, the sensing layer includes the redox polymer, electrically connecting the thermostable peroxidase (first enzyme) to the electrode, and also includes the peroxide-generating enzyme (second enzyme), the redox centers of which are not electrically connected to the redox polymer or to the electrode.

Alternatively, the peroxide-generating enzyme layer 24 can be formed directly over the sensing layer 21 (see FIGS. 20 and 21), but only when the peroxide-generating enzyme is intrinsically insulated or immobilized in an electrically insulating matrix. If the $H_2O_2$ generating enzyme is neither intrinsically insulating nor immobilized in an insulating matrix, an $H_2O_2$-permeable, electrically insulating layer 12 can be placed between the sensing layer 11 and the peroxide-generating (second) enzyme layer 13 to achieve the desired insulation.

The peroxide-generating (second) enzyme layer is formed by any of the following methods. Particles, such as silica-containing particles in which the second enzyme is stabilized, can be dispersed in a polymer, such as a silicone rubber solution or silicone rubber precursor solution. A droplet of this mixture is then applied to the working electrode. Alternatively, the peroxide-generating layer is formed by adding a cross-linking agent to the second enzyme and applying a droplet containing the second enzyme and its crosslinker to the working electrode. Useful cross-linking agents include, for example, poly(ethylene glycol) diglycidyl ether (PEGDGE). For cross-linking of glycoproteins such as glucose oxidase, the enzyme is oxidized with $NaIO_4$, forming reactive aldehyde functions condensing with surface amines, such as those of enzyme lysines. The preferred method for producing a peroxide-generating layer containing glucose oxidase, when the enzyme is not immobilized in a silica sol-gel, is the latter, $NaIO_4$ method. For peroxide-generating layers containing lactate oxidase, which is also not immobilized in a silica sol-gel, cross-linking of its mixture with poly(N-vinyl imidazole) with PEGDGE is preferred. The second enzyme may also be immobilized with glutaraldehyde or glutaraldehyde and a protein such as albumin.

An enzyme stabilized by the silica sol gel matrix can be ground to a find powder and dispersed in a silicone, preferably in an elastomeric silicone, and most preferably in a water-based elastomeric silicone precursor. This dispersion is then applied to the thermostable peroxidase layer to form a hydrogen peroxide-generating layer. Silicone is a preferred binder in this layer due to its oxygen permeability.

Electrically Insulating Layer

Another means for preventing oxidation/reduction of the peroxide-generating (second) enzyme is the addition of an electrically insulating membrane 12 that is permeable to $H_2O_2$ between sensing layer 11 and second enzyme layer 13. The insulating membrane can be inorganic or organic, but preferably is an organic polymer such as cellulose acetate. The second enzyme may be immobilized in a layer 13 over the polymeric membrane.

Preferably, the insulating membrane 12 is permeable to the small $H_2O_2$ molecule but is not permeable to the larger, readily oxidizable, potentially interfering ascorbate, acetaminophen or urate species. Preferably, the ratio of the permeability of layer 12 to $H_2O_2$ and one or more of ascorbate, acetaminophen, and urate is greater than 2:1. Useful, selectively $H_2O_2$ permeating polymer films include dense cellulose acetate, cured Nafion™, and nylon. Using known, standard methods, dense, small pore size films of cellulose acetate or nylon are cast from cyclohexanone or tetrahydrofuran; Nafion™ films are made from alcohol and alcohol-water emulsions and curing.

Analyte-Transport Controlling Layer

If the second enzyme is not immobilized, or when it is desired to broaden the dynamic range of the sensor so that the sensor will respond, preferably linearly, to higher concentrations of the analyte, then an analyte-transport controlling layer 14 is placed between the solution that is being analyzed and second enzyme layer 13 of the sensor. This analyte-transport controlling layer 13 functions to contain the second enzyme and thereby avoid its loss, and/or to limit the flux of the analyte or second enzyme substrate to the second enzyme layer.

It is of essence that this second membrane be permeable to $O_2$, the co-reactant in the enzyme-catalyzed generation of $H_2O_2$ in the presence of the substrate. It is also of essence that the ratio of permeabilities of $O_2$ and of the substrate or its precursor through this second membrane be large enough for oxidation or dehydrogenation of the substrate in the reaction catalyzed by the second enzyme with the concurrent formation of water, a reaction whereby $O_2$ is consumed. Because the concentration of $O_3$ in saturated aqueous solutions is well below the usual concentrations of analytes such as glucose or lactate in biological fluids, including fluids in the body of animals, analyte-transport controlling layers 14 that are much more permeable to $O_2$ than to the substrate or its precursor are preferred.

Generally, membranes or polymers for which the permeability coefficient of molecular oxygen is greater than $10^{-8}$ cm$^3$ (STP) cm cm$^{-2}$s$^{-1}$ (cm Hg)$^{-1}$ at 25° C. are preferred. (Explanation of the permeability units is given in *Polymer Handbook, Second Edition,* J. Pandrup and E. H. Immergut, Editors, John Wiley & Sons, New York, 1975, pages III-229–231.) Polymers for use in the analyte-transport controlling layer 14 are those that are highly permeable to $O_2$, preferably those in which the ratio of $O_2$ and substrate (or substrate precursor) permeabilities is greater than 10:1, and more preferably greater than 100:1. It is well known that the permeability of $O_2$ in silicones, for example in silicone rubbers, formed by cross-linking poly(dimethyl siloxanes), is particularly high. Thus, silicones are useful polymers for this layer. Another useful material is cellulose acetate.

Biocompatible Layer

For in vivo use, the sensor is preferably coated with a biocompatible film 15 that is permeable to the substrate converted in the reaction catalyzed by the second enzyme. This biocompatible film is placed on the solution side of the sensor.

The preferred biocompatible layer 15 is formed of a hydrogel, e.g., a polymeric composition which contains more than 20% by weight of water when in equilibrium with a physiological environment such as living tissue or blood. An example is a cross-linked derrivative of polyethylene oxide, e.g., a tetraacrylated derrivative of polyethylene oxide. The polymeric compositions are non-toxic, non-immunogenic, non-thrombogenic, and otherwise compatible with living tissue of animals.

A biocompatible layer 15 is not necessary if the analyte-transport controlling layer 14 or the second enzyme layer 13 are biocompatible. For example, many solid silicones are biocompatible and therefore require no additional biocompatible layer (see FIG. 20, in contrast the embodiment of the invention shown in FIG. 21 includes a biocompatible layer 25).

Stability of the Sensor

An important performance criterion of the inventive sensor is the rate of loss of sensitivity. This rate depends on the concentration of the analyte, because loss in sensitivity is usually first noticed at high analyte concentrations. At higher analyte concentrations, where complete conversion of the incoming analyte flux to $H_2O_2$ requires the presence of more of the active second enzyme, the system is very sensitive to inadequate substrate conversion in the second enzyme layer. The rate of loss of sensitivity can be reduced, even when the second enzyme is not particularly thermostable, by limiting the flux of analyte to the second enzyme layer 13 by using an analyte-transport controlling layer 14 and limiting thereby the analyte concentration.

Loss of sensitivity can also be limited and even avoided for a period of days or weeks, by incorporating in the second enzyme layer a large amount of enzyme that even if part of it becomes inactive, all of the analyte flux is still transduced by the remaining second enzyme into an $H_2O_2$ flux. If a thermostable second enzyme, such as an enzyme entrapped in an inorganic polymeric matrix, is used to form the second enzyme layer 13, sensors of unprecedentedly good stability and long life can be built and can be further improved either by incorporating a large excess of the thermostable second enzyme, much more than needed to convert the analyte flux into an $H_2O_2$ flux, or by limiting the analyte flux, or by using both techniques cooperatively.

The preferred sensors are also stable for long periods of time at temperatures of 37° C. or greater. Preferably, the sensor is stable for 100 hours or more at this temperature with a drop in the sensor's output of 10% or less. Preferably, the sensor and the enzymes within the sensor are stable at 30° C., more preferably at 40° C., and most preferably at 50° C. or 60° C. or higher.

Other Sensors

Many of the principles of the invention can be used in sensors other than the peroxidase sensors described hereinabove. In particular, the immobilization of a second enzyme in an inorganic polymeric matrix formed using the sol-gel process can be used effectively in the enzyme sensor described in U.S. Pat. No. 5,593,852 herein incorporated by reference. In the sensor, a layered structure similar to that depicted in FIGS. 19–21 is used. However, in the sensing layer an analyte-sensitive enzyme is used rather than a peroxidase. For example, glucose oxidase or glucose dehydrogenase is present in the sensing layer if the analyte is glucose or lactate oxidase is used if the analyte is lactate.

These sensors often have a second enzyme layer which is functions as an interferent-eliminating layer. This layer contains one or more enzymes which catalyze reactions of interferents, such as ascorbate, urate, acetaminophen. Enzymes for use in this layer include peroxidases and lactate oxidase (when glucose is the analyte) or glucose oxidase (when lactate is the analyte). These enzymes can be immobilized in an inorganic polymeric matrix as described hereinabove and used to form a second enzyme layer. Furthermore, these enzymes may be stabilized by immobilization in the inorganic polymeric matrix either alone or in conjunction with a polyelectrolytic polymer as described hereinabove.

EXAMPLES

The invention will be further defined by reference to the following Examples. These examples are not intended to limit the scope of the invention, but rather to illustrate some of the invention's specific embodiments.

Example 1

Preparation of 4-layered Sensors

Soybean peroxidase (SBP) was obtained from Harlan Bioproducts for Science, Indianapolis, Ind., High grade, 130 pyrogallol units/mg (Cat. No: SP04 Lot No: SPLO515). The lactate oxidase (LOx) was obtained from Genzyme, Boston, Mass., Lot # D50293, Cat. # 70-1381-01, EC 1.1.2.3 from *Acerococcus viridans*, 37.0 units/mg of powder. Poly (ethylene glycol) diglycidyl ether (PEGDGE) was obtained from Polysciences, Inc., Warrington, Pa. A 30% hydrogen peroxide solution was obtained from Aldrich, and diluted solutions were prepared daily.

Electrodes

Vitreous carbon electrodes, 3 mm in diameter, were polished and cleaned using 3 grades of alumina slurry: 5, 1, and 0.3 microns, with sonication and rinsing between grades. Each polished and cleaned electrode was tested in PBS by scanning the potentials of interest (−0.4 V to +0.4V vs. SCE) to ensure that the electrochemistry was featureless. The four-layered sensors were prepared as follows:

Hydrogen Peroxide Sensing Layer

A redox polymer, PVP-bpy-Os (or POs-EA.), was synthesized by partially complexing the pyridine nitrogens of poly-(4-vinylpyridine) with $Os(bpy)_2Cl^{+/+2}$, and then partially quaternizing the resulting polymer with 2-bromoethylamine, by the method described in Gregg and Heller, 1991, *J Phys. Chem.* 95:5970. The osmium-containing redox centers allow for electrical communication between the carbon surface and the peroxidase heme centers, and the pyridinium-N-ethylamine functions enhance hydration and provide primary amines for cross-linking. The ratio of unmodified pyridines to osmium-complexed pyridines to ethylamine quarternized pyridines was 3.3:1.0:0.8.

The first layer, the hydrogen peroxide sensing layer, was prepared by placing droplets of 2 μl PVP-bpy-Os (5 mg/ml), 2 μl soybean peroxidase (5 mg/ml), and 1 μl of the crosslinker PEGDGE (2.5 mg/ml) on the carbon surface. The droplets were mixed on the surface of the electrode with the tip of a syringe. The electrode was then allowed to dry for 16 hours at room temperature. The resulting dark purple film appeared to be well spread and uniform. The dried electrode was washed in PBS for 20 minutes at 1000 rpm, rinsed with water, and permitted to dry at room temperature.

Hydrogen Peroxide Transport-Limiting Layer

To prepare the second layer, 4 μl of 0.5% cellulose acetate (Sigma, approximately 40% acetate content) in cyclohexanone (Aldrich) was placed atop the dried and washed hydrogen peroxide sensing layer. The electrode was permitted to dry for two hours at room temperature. The resulting film appeared to be well spread and uniform.

Second Enzyme Layer (Without Sol-gel Silica)

To immobilize the glucose oxidase (GOx) enzyme, two different immobilization procedures were used. For GOx, a solution of 100 μl of 20 mg/ml of GOx in water was prepared. Glucose oxidase (GOx) was obtained from Sigma, ED 1.1.3.4 from *Aspergillus niger* type X-S, 198 units/mg solid, 75% protein. After the addition of 50 μl of 12 mg/ml $NaIO_4$ in water, the enzyme-periodate solution was incubated at room temperature and in the dark for two hours, following the procedure described in Vreeke et.al., 1995, *Anal Chem.* 67:4247. A volume of 4 μl of the incubated mixture was placed atop the cellulose acetate film to form an immobilized GOx analyte sensing layer, which was permitted to dry overnight.

For LOx, a mixture of 10 μl of 20 mg/ml LOx, 20 μl of 10 mg/ml PVI, and 10 μl of 5 mg/ml PEGDGE in water was prepared. A volume of 4 μl of the LOx mixture was placed atop the cellulose acetate film to form an immobilized LOx analyte sensing layer, which was permitted to dry overnight.

Analyte Transport-Limiting Layer

The fourth polymeric layer, an analyte transport-limiting layer of cellulose acetate, was prepared and applied to the analyte sensing layer as described above for the hydrogen peroxide transport-limiting layer. A volume of 4 μl of 0.5% cellulose acetate in cyclohexanone was placed atop the immobilized oxidase layer (analyte sensing layer), and permitted to dry for two hours.

The four-layered electrode was then washed in PBS for 25 minutes and rinsed with water.

Example 2

Varying Amounts of Soybean Peroxidase

The 4-layered electrodes were prepared as described for Example 1, but varying the enzyme weight fraction of soybean peroxidase in the crosslinked redox polymer of the hydrogen peroxide sensing layer or by varying the total loading of SBP. Current measurements were collected using a Princeton Applied Research model 273 potentiostat/galvanostat in a 3-electrode cell. All measurements were performed using a 20 mM phosphate buffer (pH 7.3) containing 0.1 M NaCl, except measurements in which pH dependence was studied. In experiments where pH was varied, 2M solutions of HCl or NaOH were added to the phosphate buffer solution.

Glucose and lactate solutions were prepared by diluting a stock 2M solution in phosphate buffer. All experiments were run at 37° C. under air in 100 ml of phosphate buffer, unless otherwise indicated. The cell contained a rotating glassy carbon working electrode, a saturated calomel reference electrode (SCE), and a platinum counter electrode, isolated from the bulk solution by a Vycor™ frit. The stability measurements were run in a stirred cell, the rotating disk experiments were performed using a Pine RDE4 potentiostat, with an MSRX speed controller, an X-Y-Y' plotter, and a VWR 1165 refrigerated constant temperature circulator. The rotating electrode experiments were performed at 1000 rpm, unless otherwise noted.

Figure 1:
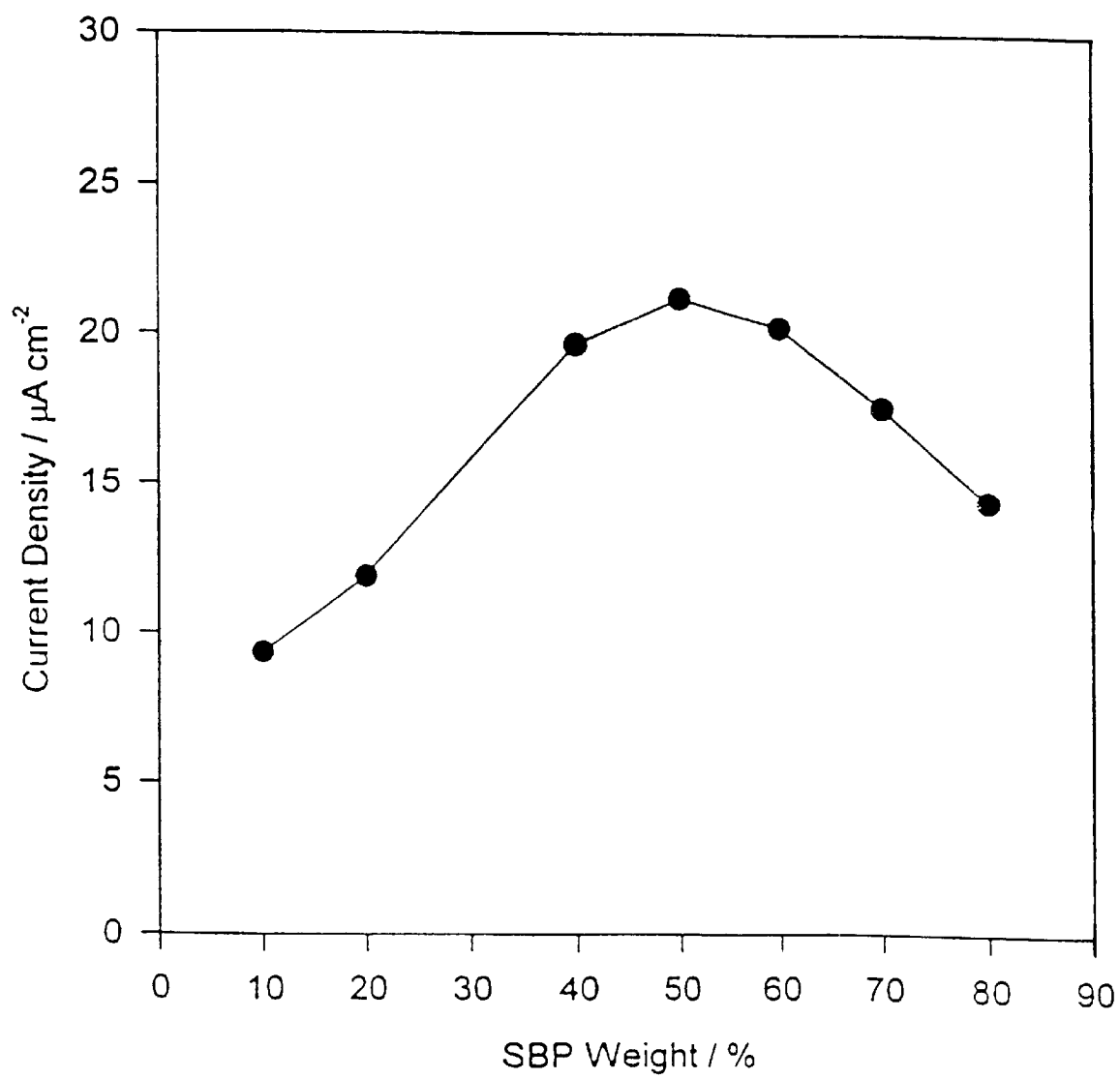
FIG. 1 is a graph showing the dependence of current density on the weight fraction of the thermostable peroxidase in the sensing layer at 60 $\mu$g cm$^{-2}$ loading (16 mM glucose, 1000 rpm, 37° C., pH7.3, in air, 0.00V (SCE))

Results:

As shown in FIG. 1, for a given mass of redox polymer (POsEA), the current density peaked between 40 wt % and 60 wt % of SBP. For a 50 wt % electrode, the current density reached a plateau at a loading of 60 $\mu g/cm^2$. Although current densities were independent of loading above 60 $\mu g/cm^2$, the response times increased with increased loading. For this reason, the preferred sensing layer contained 50 wt % SBP at a total loading of 60 $\mu g/cm^2$.

Figure 2:
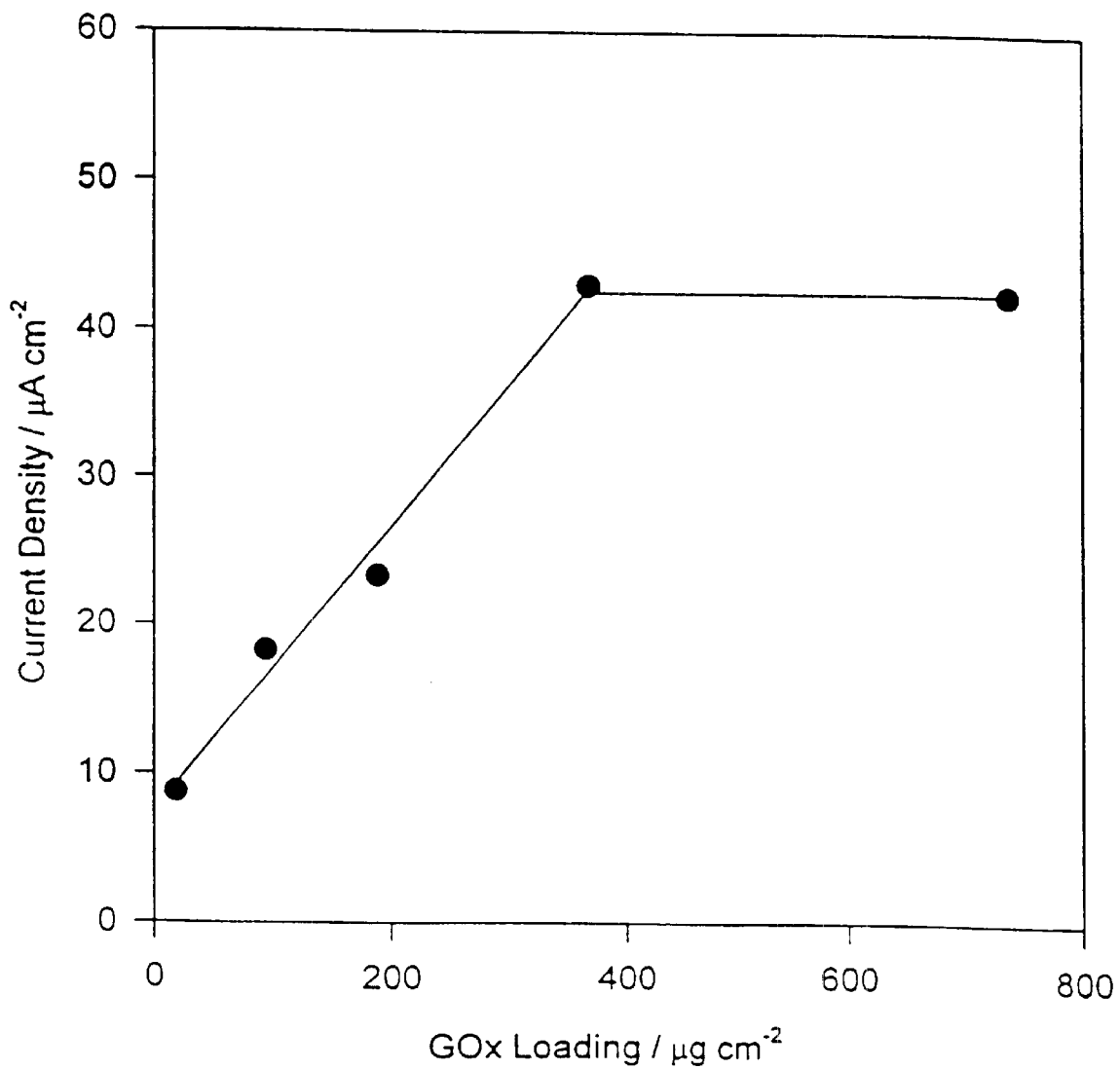
FIG. 2 is a graph showing the dependence of the electroreduction current density on the GOx loading (16 mM glucose, 1000 rpm, 37° C., pH7.3, in air, 0.00V (SCE))

FIG. 2 shows the dependence of current densities on the amount of glucose oxidase immobilized on the electrode. The current densities at 4 mM glucose reached a plateau at GOx loadings of 375 $\mu g/cm^2$. Electrodes made with LOx exhibited similar behavior with a current density plateau at a loading of 600 µg/cm².

Example 3

Varying Thickness of First Transport-controlling Layer and Fourth Analyte-transport-limiting Layer The hydrogen peroxide transport-controlling layer functions to control the transport of hydrogen peroxide from the analyte sensing layer to the hydrogen peroxide sensing layer. This layer also serves to electrically isolate the POsEA of the hydrogen peroxide sensing layer from the immobilized oxidase layer, that is, to prevent "short-circuiting" of the sensor through "wiring" of the oxidase.

When the immobilized oxidase of the analyte sensing layer is not sufficiently insulated from the hydrogen peroxide sensing layer, redox centers of the oxidase and osmium centers of the POs-EA are electrically connected. This results in the "short-circuiting" of the electrodes. As described in Vreeke and Rocca, 1996, *Electroanalysis* 8:55, a symptom of "short-circuiting", which is often seen only at high substrate concentrations, is the suppression of the catalytic reduction current upon increasing substrate concentration. In the present experiments, "short circuiting" was diagnosed by poising the electrode at +0.5 V (SCE), where the hydrogen peroxide was not catalytically electroreduced on the "wired" peroxidase layer, and injecting 10 mM substrate. Flow of an oxidation current indicated that the electrode had a short circuit.

In the electrodes of Example 1 formed with application of 4 µl of 0.25% cellulose acetate, "short circuiting" by "wiring" of the oxidase by POsEA was effectively prevented, in contrast to electrodes prepared with thinner cellulose acetate films. (data not shown). Electrodes made without the inner cellulose acetate layer invariably exhibited short-circuiting, and the effect was often quite substantial. For example, a typical glucose electrode made without this insulating layer showed current suppression at concentrations higher than 1 mM glucose, and the current was suppressed to less than 50% of its maximum value at a concentration of 20 mM. This observation demonstrates the necessity of the insulating layer in this type of sensor.

Membranes, having a range of thickness, were obtained by using solutions of different cellulose acetate concentrations, and applying various volumes of these. The thinnest membranes were made by applying 1 µl of 0.25 weight % cellulose acetate. The thickest membranes were made by applying 4 µl of 0.5 weight % cellulose acetate solution to the surface.

While the presence of the inner cellulose acetate layer effectively prevented short-circuiting, the sensitivity of the electrodes dropped by about 50%. The sensitivity loss is attributed to less efficient collection of the $H_2O_2$ generated by the oxidase-catalyzed reaction.

Figure 3:
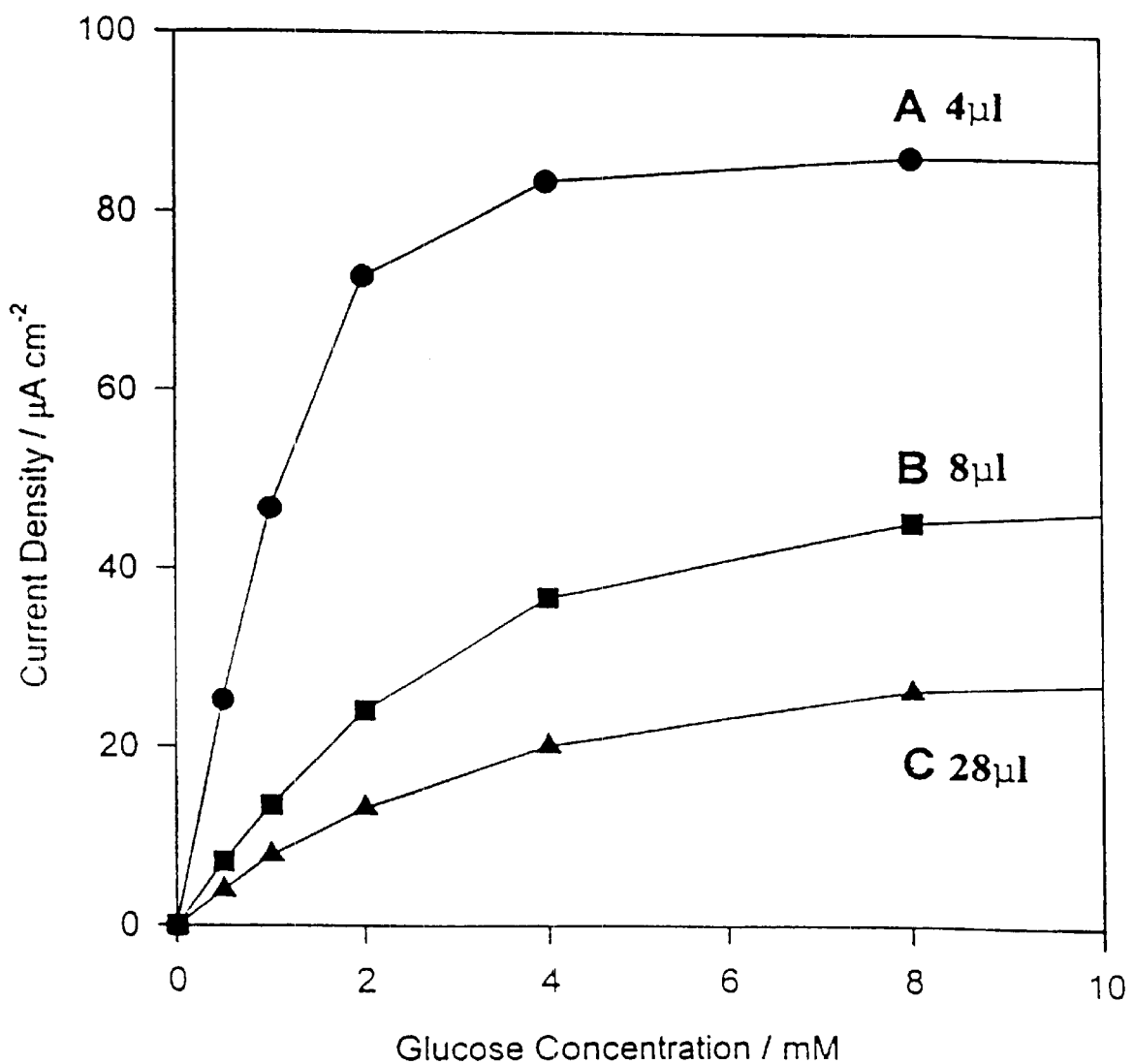
FIG. 3 is a graph showing the dependence of the calibration curves on the thickness of the cellulose acetate layer between the sensing layer and the immobilized glucose oxidase film. (A) 4 $\mu$l, (B) 8 $\mu$l, and (C) 28 $\mu$l of 0.25% cellulose acetate (16 mM glucose, 1000 rpm, 37° C. pH7.3, in air, 0.00V (SCE))

An analyte transport-limiting layer forms a fourth polymeric layer. As described for Example 1, this layer was made of cellulose acetate, and provides substrate transport control, thereby defining the dynamic range of the sensor. Increasing the thickness of the outer cellulose acetate layer decreased the sensor's sensitivity, but increased the apparent $K_m$. FIG. 3 shows the response of an electrode over-coated with varying amounts of cellulose acetate: (A) 4 µl; (B) 8 µl; (C) 28 µl of 0.25% cellulose acetate. Increasing the thickness of the outer cellulose acetate layer from 4 µl (A) of 0.25% cellulose acetate to 8 µl (B) decreased the sensitivity by 50%, but increased the apparent $K_m$ from 1 mM to 2 mM glucose. The response time ($t_{10/90}$) for electrodes with an outer cellulose acetate layer of 8 µl of 0.25% was less than 2 minutes.

Example 4

Potential Dependence of the Electrodes

The redox polymer of the electrodes of Example 1, POs-EA, has a formal redox potential of +278 mV (vs. SCE). (Gregg and Heller, 1991, *J. Phys. Chem.* 95:5970) FIG. 4 shows the dependence of current density on the applied potential for a glucose electrode of Example 1. Between 0.20 V and +0.35 V (vs. SCE), the current density was independent of applied potential. At applied potentials positive of +0.40 V, a reduction current was no longer observed. At applied potentials more negative than −0.20 V, oxygen reduction effects are observed.

Example 5

Oxygen Dependence of the Electrodes

In nature, the reduced form of an oxidase requires oxygen for reoxidation and production of hydrogen peroxide. FIG. 5 shows the dependence of the current density on the partial pressure of the dissolved oxygen for the electrodes of Example 1. At 37 C, the concentration of oxygen in an air-saturated aqueous solution is about 0.2 mM (See, Hodgman Ind.: *Handbook of Chemistry and Physics*, 44th Ed, The Chemical Rubber Publishing Co., Cleveland, Ohio, 1963, page 1706).

For glucose electrodes, even at very low oxygen concentrations, the current densities were lower only by about 20% than those in oxygen saturated solutions. For oxygen concentrations of 0.04 mM or higher, i.e., in solutions saturated with atmospheric pressure argon containing only 4 volume % oxygen, the current density was independent of the oxygen concentration.

For lactate electrodes, however, at low oxygen partial pressures, the dependence of current density on oxygen concentration was more substantial. This difference is explained by the different immobilization methods for GOx and LOx. The sodium periodate crosslinked GOx layer has lower oxygen permeability than that of the PEGDGE crosslinked PVI-LOx layer. At high (5 mM) lactate concentrations, the current density became independent of the partial pressure of oxygen only when the volume % of oxygen reached its volume % in air (21%). For lower lactate concentrations, it is expected that the current will be less dependent on oxygen partial pressure as a lower oxygen flux suffices for the quantitative conversion of lactate to hydrogen peroxide and pyruvate.

Example 6

Salt and pH Dependence of the Electrodes

FIG. 6 shows the dependence of current density on the concentration of NaCl for both GOx (A) and LOx (B) electrodes of Example 1. Although the current densities were somewhat higher at low salt concentrations, the electrodes were virtually insensitive to salt concentrations up to 1M NaCl. Increasing the salt concentration from 0.1M to 1M decreased the current density by less than 10%.

FIGS. 7A and 7B show the dependence of the current density on pH for both GOx (FIG. 7A) and LOx (FIG. 7B) electrodes of Example 1. For the glucose electrodes, the current density was near its maximum between pH 4.5 and pH 6.5, the plateau matching the pH dependence of GOx activity in solution, which exhibits maximal activity near pH 5.5. For lactate electrodes, the current density reached its maximum at pH 4.0, differing from the pH dependence of LOx activity in solution, which exhibits maximal activity at pH 6.5. Both glucose and lactate electrodes were irreversibly deactivated below pH 3.0.

Example 7

Rotation Rate and Temperature Dependence

FIG. 8 shows the dependence of current density on the angular velocity of the rotating electrodes for both GOx (A) and LOx (B). The current density was practically independent of rotation rate. For example, in the case of the glucose electrode, increasing the rotation rate from 50 rpm to 1000 rpm increased the current density by less than 5%.

FIGS. 9A and 9B show the dependence of the current density on temperature for both electrodes, FIG. 9A shows data for 5 mM glucose; and FIG. 9B shows data for 5 mM lactate.

Example 8

Long Term Operational Stability

The stability of the current density of the sensors of Example 1 during continuous operation at 37° C. was a strong function of oxidase loading. As shown in FIG. 10A, the higher the GOx loading, the better the operational stability at 37° C. An electrode loaded with 1.3 μg of GOx (a) had an operational half life of 40 hours, while an electrode loaded with 52 μg of GOx (d) maintained 100% of its initial current density for over 100 hours and lost only 10% of its initial current density after 200 hours, and less than 25% after 280 hours. FIG. 11 shows the current response before and after the long term operational stability experiments for glucose electrodes at both high and low loadings. While the electrode with a 1.3 μg GOx loading lost more than 90% of its current density at all glucose concentrations after 100 hours of operation at 37° C., the electrode with 26 μg GOx loading demonstrated no loss of current density at low concentrations, and a loss of only 25% of current density at glucose concentrations greater than 5 mM after 200 hours of operation. Cyclic voltammetry revealed that the electrodes did not lose electroactive osmium throughout the long term stability experiments (FIG. 12), and operational stability was maintained as long as the amount of active enzyme sufficed to oxidize all of the glucose flux.

Similarly, FIG. 10(B) shows that the higher the LOx loading, the better the operational stability at 37 C. While the electrode with a 20 μg LOx loading lost more than 80% of its current density at all lactate concentrations after 120 hours of continuous operation at 37 C, the electrode with 160 μg LOx loading demonstrated no loss of current density at low concentrations, and a loss of only 10% of current density at lactate concentrations greater than 5 mM after 160 hours of operation. Cyclic voltammetry revealed that the electrodes did not lose electroactive osmium throughout the long term stability experiments, and operational stability was maintained as long as the amount of active enzyme sufficed to oxidize all of the lactate flux (data not shown).

Example 9

Selectivity Against Interferents

Interferents such as ascorbate, urate, and acetaminophen are oxidized at POsEA coated carbon electrodes. These interferents decrease the catalytic hydrogen peroxide electroreduction current. Nevertheless, no current change was observed with the electrodes of Example 1, upon the addition of urate up to 0.5 mM or acetaminophen up to 1.0 mM, both in the presence and absence of substrate. Ascorbate was electrooxidized only at a negligibly slow rate. For example, at 1 mM glucose, an injection of 0.1 mM ascorbate caused a decrease of less than 1% in the current density, and, at 64 mM glucose, injection of 0.1 mM ascorbate caused a decrease of less than 0.1% in the current density.

Example 10

Preparation and Activity Test for Lactate Oxidase-doped Silica Gel Powder

Preparation of PVI-LOx-doped Silica Gel Powder 0.15 g of tetramethylorthosilicate (TMOS, Cat. # 34,143–6, Aldrich, Milwaukee, Wis.) was added to a small vial. The vial was placed into an ice-bath, and stirred at approximately 600 rpm. 36 mL of 2.44 mM HCl was added and the solution was stirred for 10 min. A vacuum was then applied to the vial for an additional 10 minutes to eliminate the methanol produced in the sol process. The vacuum was released, and pH of the solution was adjusted to pH 5.1 by adding 20 mL of 20 mM phosphate buffer (pH 7.4).

In separate small vial, 6 mg of lactate oxidase (LOx, from aerococcous viridens, 41 units/mg, Cat. #1381, Genzyme, Cambridge, Mass.). 180 mL of 10 mM 4-(2-hydroxyethel)-1-piperazineethane-sulfonic acid (HEPES) buffer solution (pH 7.5), and 20 mL of 20 mg/mL of aqueous poly(1-vinylimidazole) were mixed as described by Timothy J. Ohara, Ravi Rajagopalan and Adam Heller, *Anal. Chem.* 1994, 66, 2451–57. This solution was added to the TMOS-containing solution and was stirred for 1 minute. A vacuum was applied to the stirred mixture until a gel formed. The vacuum was released and the gel was rinsed with 2 mL of distilled water three times. The gel was then soaked in 2 mL of distilled water overnight at 4° C. The water was removed from the vial and the gel was allowed to dry at room temperature overnight. The dried gel was collected and ground to a powder with a mortar and pestle.

Qualitative Activity Test for PVI-LOx-doped Silica Gel Powder

For a qualitative activity test of lactate oxidase-doped silica gel at room temperature, peroxide test strips (Reflectoquant® 16974 Peroxide Test, Merck, Darmstadt, Germany) were used. 1–2 mg of lactate oxidase-doped silica gel powder was applied to the active area of the test strip. 20 μL of 1 M lactate (prepared in phosphate buffer solution, pH 7.4) was applied to the same area of the test strip. The presence of lactate oxidase activity was indicated by the appearance of a blue color on the active area of the strip.

Quantitative Activity Test for PVI-LOx-doped Silica Gel Powder

In the presence of oxygen, a lactate oxidase catalyzes the oxidation of lactate to pyruvate. In the process, hydrogen peroxide is formed stoichiometrically. The enzymatically formed hydrogen peroxide can be quantitatively measured using a peroxidase linked assay system, which causes the formation of a quinoneimine dye. This dye can be measured spectrophotometrically at 564 nm.

Preparation of Solutions for PVI-LOx-doped Silica Gel Powder Activity Test

Reaction mixture I was prepared by combining the following solutions:

(a) 6.0 mL 0.2 M 3,3-dimethylglutarate [$HO_2CCH_2CH_2C(CH_3)_2CO_2H$]—NaOH buffer, pH 6.5;

(b) 3.0 mL peroxidase (from horseradish, Sigma Chemical Inc, St. Louis, Mo.), 50 units/mL in water;
(c) 3.0 mL 15 mM 4-aminoantipyrine in water;
(d) 3.0 mL 0.5 M substrate; and
(e) 9.0 mL distilled water.

A stock solution of 0.5% N,N'-dimethylaniline was prepared by mixing 0.2 g into 100 mL of water. A stock solution of the enzyme diluent was prepared by adding 66 mg of FAD into 4 mL of a 10 mnM $KH_2PO_4$—NaOH buffer solution, pH 7.0. Lactate oxidase solutions were prepared at a concentration of 1 mg/mL in enzyme diluent. A stock solution of enzymatic reaction stopper was prepared by dissolving 0.25 g of dodecylbenzenesulfonic acid sodium salt [$C_{12}H_{25}C_6H_4SO_3Na$] in 100 mL of distilled water. All chemicals were purchased from Aldrich Chemical Company (Milwaukee, Wis.) unless otherwise mentioned.

Activity Test Procedure for PVI-LOx-doped Silica Gel Powder 1.0 mg of lactate oxidase-doped silica gel powder was weighed into a 3 mL cuvette. 100 μL of distilled water was used to wash the powder down from the inside walls to the bottom of the cuvette. The cuvette was then capped with parafilm and placed in a temperature bath set at 63° C. for the experimental period of time. After this period of time, the cuvette was removed from the bath, and 100 μL of enzyme diluent was added. The cuvette was then placed into a 37° C. temperature bath for another five minutes.

A solution with a 4:1 ratio of reaction mixture I to 0.5% dimethylaniline was prepared and allowed to equilibrate at 37° C. One milliliter of this solution was added to the cuvette. This mixture was agitated and allowed to react for exactly 10 minutes at 37° C. Immediately after this incubation, 2.0 mL of the reaction stopper were added and the absorbance at 564 nm (As) was measured.

The procedure was repeated, using 1.0 mg of enzyme-free silica gel powder in place of the lactate oxidase-doped silica gel powder. The same procedure was followed thereafter and the blank absorbance (Ab) was measured. Therefore, the net absorbance of the lactate oxidase-doped silica gel powder was determined by ΔA (ΔA=As−Ab). If ΔA was greater than 0.6, the assay was repeated, and the weight of the lactate oxidase-doped silica gel powder was adjusted accordingly.

Results for PVI-LOx-doped Silica Gel Powder

FIG. 13 shows the activity decrease of lactate oxidase in solution over time. The enzyme had a half-life of 6.8 minutes at 63° C., which was in agreement with the previously published value (H. Minagawa, N. Nakayama, and S. Nakamoto, 1995, *Biotechnology Letters* 17(9):975).

FIGS. 14A and 14B show the comparison of the enzyme activity loss of PVI-lactate oxidase-doped silica gel powder with that of lactate oxidase-doped silica gel powder at 63° C. FIG. 14A shows PVI-lactate oxidase-doped silica gel. FIG. 14B compares PVI-lactate oxidase-doped silica gel (a) with lactate oxidase-doped silica gel (b). At 63° C., the LOx-doped silica gel powder (b) had the same half-life as that of LOx in solution. However, the PVI-LOx-doped silica gel powder FIG. 14B(a) and FIG. 14A maintained 60% of its initial activity after 900 minutes at 63° C.

FIG. 15 shows the time dependence of the activity loss for lactate oxidase in different environments at 50° C. At this temperature, the PVI-LOx-doped silica gel powder (A) maintained 85% of its initial activity after 120 hours, whereas the LOx-doped silica gel powder (C) had a half-life of only 10 hours. Both the LOx in solution (D) and the PVI-LOx in solution (C) demonstrated a half-life of less than one hour at this temperature.

The PVI-LOx-doped silica gel powder maintained 100% of its initial activity after 11 days of soaking in water at room temperature.

Example 11
Preparation and Activity Test for Glucose Oxidase-doped Silica Gel Powder Preparation of GOx-doped Silica Gel 1.527 g of tetramethylorthosilicate(TMOS) was added to a small vial. The vial was placed into an ice-bath, and the solution was stirred at approximately 600 rpm. 360 mL of 2.44 mM HCl was added and the solution was stirred for 10 min. A vacuum was applied to the vial for an additional 10 minutes to eliminate the methanol produced in the sol process. The vacuum was released and the pH of the solution was adjusted to pH 5.1 by adding 100 mL of 20 mM phosphate buffer (pH 7.4). In a separate small vial, 67 mg of glucose oxidase (GOx from *Aspergillus niger*, Cat. # G-7141, 183 units/mg, from Sigma, St. Louis, Mo.) and 540 mL of 10 mM 4-(2-hydroxyethyl)-1-piperazineethanesulfonic acid (HEPES) buffer solution (pH 7.5) were mixed. This solution was added to the TMOS-containing solution and was stirred for 1 minute. A vacuum was applied to the stirred mixture until a gel formed. The vacuum was released, and the gel was allowed to dry overnight at room temperature. The dried gel was first collected and then ground to a powder with a mortar and pestle.

Qualitative Activity Test for GOx-doped Silica Gel

For a qualitative activity test of glucose oxidase-doped silica gel at room temperature, peroxide test strips (Reflectoquant® 16974 Peroxide Test, Merck, Darmstadt, Germany) were used. 1–2 mg of glucose oxidase-doped silica gel powder was applied to the active area of the test strip. 20 μL of 1 M glucose (prepared in phosphate buffer solution, pH 7.4) was applied to the same area of the test strip. The presence of glucose oxidase activity was indicated by the appearance of a blue color on the active area of the strip.

In order to test the activity of the glucose oxidase-doped silica gel powder at higher temperatures, the powder was immobilized onto a glass slide according to the following procedure. 26 mg of Bermocoll® EHM-100 (Berol Nobel AB, Stenungsund, Sweden), 1 mL of cyclohexanone and 1 mL of water were mixed in a small vial. The vial was heated and agitated over a flame for 5 minutes. The solution was allowed to settle and the white micelle fraction was collected. 90 μL of the micelles and 10 mg of the glucose oxidase-doped silica gel powder were mixed and then stirred for 5 minutes. 10 μL of the mixture was applied to a glass slide and allowed to dry overnight. The glass slide was immersed in a temperature bath for 5 minutes at the experimental temperature. The slide was removed and allowed to dry. 10 μL of 2 M glucose was applied to the immobilized micelles. The active area of the peroxide testing strip was placed on top of the immobilized micelle area. The appearance of a blue color on the strip indicated the presence of glucose oxidase activity.

Quantitative Activity Test for GOx-doped Silica Gel

The quantitative activity test of glucose oxidase was performed exactly as that for lactate oxidase except a 1 M glucose solution was used in place of the 1 M lactate solution and glucose oxidase-doped silica gel powder was used in place of lactate oxidase-doped silica gel powder.

Qualitative Results for GOx-doped Silica Gel

The glucose oxidase-doped silica gel powder retained activity after immersion in water for 5 minutes at 40, 50, 60, 70, 84, and 92° C., while similarly immobilized glucose oxidase in DAEA Dextran, Heparin, Lactitol, Gafquats, and Dextran Sulfate showed no activity retention at temperatures higher than 70° C.

The glucose oxidase-doped silica gel powder was then tested for activity at 92° C. for longer time periods. Activity was retained for up to 20 minutes, after which, the micelles washed off of the slides. At 75° C., activity was retained for over 60 minutes.

Quantitative Results for GOx-doped Silica Gel

FIG. 16 shows the comparison of the enzyme activity loss of glucose oxidase-doped silica gel powder (B) with that of glucose oxidase in solution (A) at 63° C. At this temperature, the GOx-doped silica gel powder (B) maintained 60% of its initial activity after 1200 minutes, while the half-life of GOx in solution (A) was 6.5 minutes, as shown in the figure inset.

Example 12

Preparation and Activity Test for PEI-LOx-doped Silica Gel

Polyethyleneimine (PEI) is chemically similar to PVI and has been shown to stabilize enzymes. PEI-LOx-doped silica gel powder was prepared according to the same procedure as that for PVI-LOx-doped silica gel powder. FIG. 17 shows the activity loss over time of PEI-LOx-doped silica gel powder at 63° C. After 900 minutes, the PEI-LOx-doped silica gel powder maintained 18% of its initial activity.

Example 13

Preparation and Activity Test of PVI-LOx Adsorbed onto Colloidal Silica

PVI-LOx was also adsorbed onto colloidal silica according to the following procedure. 1.69 mg of LOx was dissolved in 23 μL of 20 mg/mL of PVI. This solution was mixed with 33 μL of colloidal silica (34 wt. % suspension in water, Aldrich, Milwaukee, Wis.). The resulting solution was allowed to dry. The solid was first collected and then ground to a powder in a mortar and pestle. The PVI-LOx adsorbed silica had the same half-life as LOx in solution at 63° C.

Example 14

Layered Sensor with Sol-Gel Silica Immobilized GOX Particles in Silicone

A 0.29 mm polyimide insulated gold wire (polyimide insulation thickness 0.02 mm, gold wire OD 0.25 mm) was etched galvanostatically in a KCN solution as described by E. Csöregi et.al., *Anaytical. Chemistry* 66:3131–3138, 1994, to form about 100 μm deep recess. The following sequence of droplets were deposited in the recess to form a four-layered structure. The innermost layer contained a hydrogen peroxide-sensing soybean peroxidase and redox polymer. The second layer was a hydrogen peroxide permeable insulating layer. The third layer was a silicone layer in which sol gel silica-immobilized glucose oxidase containing particles were dispersed. The fourth, cellulose acetate layer was oxygen permeable and glucose flux reducing.

To form these four layers on the electrode, the following procedure was used. The redox polymer solution prepared as described for Example 1 was used at a concentration of 10 mg/mL. Soybean peroxidase (SBP) in deionized water was used at a concentration of 10 mg/mL. PEGDGE was used at 5 mg/mL. The redox polymer, SBP, and PEGDGE solutions were mixed at a 2:2:1 ratio. Ten droplets of about 5 nL each of the mixed solution were sequentially deposited within the recess to form the sensing layer, which was cured at 55° C. for 20 minutes.

The solution from which the second layer, the hydrogen peroxide permeable membrane, was cast, consisted of 0.5%/ weight % cellulose acetate (40% acetylated) in cyclohexanone. One 5 nL droplet of this solution was applied to the cured sensing layer in the recess.

The hydrogen peroxide generating enzyme layer (third layer) was made of 0.5 parts of the sol-gel immobilized glucose oxidase of Example 15, 1 part of Dow Corning 3-5025 silicone water based elastomer that was thoroughly mixed and dispersed in 9 parts of water by grinding in an agate mortar for 30 minutes. Three drops of this mixture were applied on the cellulose acetate layer, and cured at 50° C. for ten minutes.

The fourth layer was made of 2 weight % cellulose acetate (40% acetylated) also containing 1.6 weight % TWEEN 80 in cyclohexane, of which one drop was applied onto the third layer.

When the electrode, produced as described above, was poised at −0.045V (SCE) in a phosphate buffer solution at pH 7.0 (20 mM phosphate, 0.14 M NaCl), the current in the absence of glucose was 0.1 nA. When the glucose concentration was brought to 5 mM, the current increased in less than 20 seconds to 3.6 nA. Further increases of the concentration to 10 mM resulted in respective currents of 6.6 nA and 8.5 nA.

Example 15

Two Layered Glucose Electrode

Recessed palladium electrodes were prepared as described by E. Csöregi et.al., *Anaytical. Chemistry* 67:1240, 1995, for gold electrodes, except that the solution in which the palladium was etched under galvanostatic control was not a potassium cyanide solution, but 6M Hcl. The recess formed was about 100 μm deep. Aqueous solutions of 10 mg/mL soybeanperoxidase, 10 mg/mL POs-EA and 5 mg/mL PEGDGE were prepared.

In a small vial, 20 μL of the peroxidase solution, 20 μL of the POs-EA solution, and 10 μL of the PEGDGE solution were mixed. 5 nL of this mixed solution were applied to the palladium surface. The solution was allowed to dry, and the application and drying steps were repeated seven times. The electrode was allowed to cure overnight at room temperature.

In a small vial, 0.1 g of Dow Corning Water Based Elastomer Silicone (#3-5025, Lot #LL059026) and 0.9 g of water were thoroughly mixed. 0.95 g of this mixture and 0.05 g of glucose oxidase-doped silica gel powder were mixed. 5 nL of this mixture were applied on top of the "wired" soybean peroxidase layer of the recessed palladium electrode. The electrode was then cured for ten minutes at 50° C.

The electrode was poised at −0.045 V (SCE) in a phosphate buffer solution at pH 7.0 (20 mM phosphate, 0.14 M NaCl) and its current was measured as a function of the glucose concentration in the solution. The apparent $K_m$ of the electrode was 5 mM glucose, i.e., half of the maximum current was reached at 5 mM glucose. The response times, i.e., the rise of the current from 10 to 90% of the maximum current, were less than one minute. The sensitivity of the electrode was 0.8 nA/mM glucose.

We claim:

1. An electrochemical hydrogen peroxide sensor comprising:

an electrode; and a thermostable peroxidase immobilized on and electrically connected to the electrode;

the sensor being capable of operation at 37°C. with less than 2% loss of sensitivity per hour of continuous operation.

2. The hydrogen peroxide sensor of claim 1, wherein the thermostable peroxidase is soybean peroxidase.

3. The hydrogen peroxide sensor of claim 1, further comprising a redox polymer disposed on the electrode and coupled to the thermostable peroxidase.

4. The hydrogen peroxide sensor of claim 3, wherein the thermostable peroxidase is crosslinked to the redox polymer.

5. The hydrogen peroxide sensor of claim 3, wherein the redox polymer comprises an osmium cation.

6. The hydrogen peroxide sensor of claim 5, wherein the osmium cations are coordinatively bound to the redox polymer.

7. The thermostable peroxidase of claim 1, wherein the peroxidase is non-leachable.

8. The hydrogen peroxide sensor of claim 1, further comprising a biocompatible layer disposed over the thermostable peroxidase and the electrode.

9. The hydrogen peroxide sensor of claim 1, further comprising a second enzyme capable of catalyzing the production of hydrogen peroxide in the presence of an analyte.

10. The hydrogen peroxide sensor of claim 9, wherein the second enzyme is disposed on the electrode but electrically insulated from the electrode.

11. The hydrogen peroxide sensor of claim 9, wherein the second enzyme is insulated from the electrode by the intrinsic protein structure of the second enzyme.

12. The hydrogen peroxide sensor of claim 9, wherein the second enzyme is insulated from the electrode by a hydrogen peroxide-permeable membrane or polymer.

13. The hydrogen peroxide sensor of claim 1, wherein the sensor is capable of operation at 50° C. with less than 5% loss of sensitivity per hour of continuous operation.

14. The hydrogen peroxide sensor of claim 13, wherein the sensor is capable of operation at 50° C. with less than 2% loss of sensitivity per hour of continuous operation.

15. The hydrogen peroxide sensor of claim 1, wherein the sensor is adapted for in vivo use.

16. The hydrogen peroxide sensor of claim 1, wherein the sensor is capable of operation at 37° C. for five days with less than 10% loss of sensitivity.

17. The hydrogen peroxide sensor of claim 1, wherein the sensor is capable of operation at 37° C. with less than 2% loss of sensitivity per hour of continuous operation with intermittent measurements of analyte concentration.

18. The hydrogen peroxide sensor of claim 1, wherein the sensor is adapted for subcutaneous implantation.

19. An electrochemical hydrogen peroxide sensor comprising:
an electrode; and
a thermostable peroxidase immobilized on and electrically coupled to the electrode;
wherein, in the presence of hydrogen peroxide, the thermostable peroxidase generates an electric signal.

20. An electrochemical sensor comprising:
an electrode;
a thermostable peroxidase disposed on the electrode; and
a redox polymer disposed on the electrode configured and arranged to couple the peroxidase to the electrode.

* * * * *